United States Patent [19]
Koester

[11] Patent Number: 6,142,630
[45] Date of Patent: Nov. 7, 2000

[54] VARIABLE FOCUS LENS SYSTEM SUCH AS FOR EXAMINATION OR TREATMENT OF TRANSPARENT OR SEMI-TRANSPARENT MATERIALS SUCH AS OCULAR TISSUE

[76] Inventor: Charles J. Koester, 60 Kent Rd., Glen Rock, N.J. 07452-2041

[21] Appl. No.: 09/306,852

[22] Filed: May 7, 1999

Related U.S. Application Data

[60] Provisional application No. 60/084,789, May 8, 1998.

[51] Int. Cl.⁷ ........................................................ A61B 3/00
[52] U.S. Cl. .............................................................. 351/219
[58] Field of Search ...................................... 351/212, 214, 351/216, 219, 233, 234, 235, 236, 246; 359/676, 677, 683

[56] References Cited

U.S. PATENT DOCUMENTS

| | | |
|---|---|---|
| 576,896 | 2/1897 | Rudolph . |
| 3,937,562 | 2/1976 | Muszumanski et al. . |
| 3,972,056 | 7/1976 | Tsujimoto et al. . |
| 4,009,928 | 3/1977 | Back . |
| 4,124,275 | 11/1978 | Uesugi . |
| 4,196,970 | 4/1980 | Macher et al. . |
| 4,270,842 | 6/1981 | Muchel et al. . |
| 4,666,256 | 5/1987 | Shimizu et al. . |
| 4,784,479 | 11/1988 | Ikemori . |
| 4,799,784 | 1/1989 | Safir . |
| 4,943,162 | 7/1990 | Sims ........................................ 351/235 |
| 4,976,535 | 12/1990 | Reis . |
| 5,032,020 | 7/1991 | Robert . |
| 5,116,115 | 5/1992 | Lange et al. . |
| 5,171,254 | 12/1992 | Sher . |
| 5,245,475 | 9/1993 | Takasugi . |
| 5,305,148 | 4/1994 | Ikemori et al. . |
| 5,359,373 | 10/1994 | Koester et al. . |
| 5,361,167 | 11/1994 | Aoki . |
| 5,418,648 | 5/1995 | Ono . |
| 5,556,417 | 9/1996 | Sher . |
| 5,696,633 | 12/1997 | Nakajima . |
| 5,757,464 | 5/1998 | Volk . |
| 5,760,950 | 6/1998 | Maly et al. . |
| 5,841,590 | 11/1998 | Sato . |

OTHER PUBLICATIONS

"Stop a Moving Target", advertisement from eyeFix, Inc.
Advertisement of Volk Optical, Ophthalmalogy, (1998).
Wilensky, "Optics of Gonioscopy", Clinical Opthamology, vol. 1, pp. 3–4, (1990).
Auran et al., "Wide Field Scanning Slit in Vivo Confocal Microscopy of Flattening–Induced Corneal Bands and Ridges", Scanning vol. 16, pp. 182–186 (1994).
Koester et al., "Clinical Microscopy of the Cornea Utilizing Optical Sectioning and a High–Numerical–Aperture Objective", J. Opt. Soc. Am. A, vol. 10, No. 7, (Jul. 1993).
Barrett et al., *Optom. Vis. Sci.*, vol. 73, pp. 482–486 (1996).
Kingslake, *Lens Design Fundamentals*, pp. 105–107 (1978).

*Primary Examiner*—George Manuel
*Attorney, Agent, or Firm*—Greenblum & Bernstein, P.L.C.

[57] ABSTRACT

Variable focus lens assembly, including a first lens group with positive optical power, a second lens group with positive optical power, and an adjuster structured to be capable of adjusting a separation between the first lens group and the second lens group. The variable focus lens assembly has a numerical aperture greater than about 0.65. A variable focus lens assembly includes a first lens group that is moveable on an axis, the first lens group being well-corrected and having a numerical aperture of at least about 0.20, and a second, fixed lens group sharing the axis of the first lens group. A distance between the first lens group and the second lens group may be varied over a range. The variable focus lens assembly has a spot size which is diffraction limited over the range of distance separating the first lens group and the second lens group. The variable focus lens assembly has a numerical aperture of at least about 0.65. Methods for examining or treating one of a transparent and a semi-transparent object with a variable focus lens assembly.

32 Claims, 21 Drawing Sheets

VARIABLE FOCUS LENS SYSTEM SUCH AS FOR EXAMINATION OR TREATMENT OF TRANSPARENT OR SEMI-TRANSPARENT MATERIALS SUCH AS OCULAR TISSUE

CROSS-REFERENCE TO RELATED APPLICATIONS

The present application claims the priority under 35 U.S.C. §119(e) of U.S. Provisional Application No. 60/084,789, filed May 8, 1998, the disclosure of which is expressly incorporated by reference herein in its entirety. The present application also expressly incorporates by reference herein the entire disclosure of U.S. application Ser. No. 09/074,402, filed May 8, 1998.

GOVERNMENT LICENSE RIGHTS

The U.S. Government has a paid-up license in this invention and the right in limited circumstances to require the patent owner to license others on reasonable terms as provided for by the terms of Grant No. 1 R43 EY11808-01 awarded by National Institute of Health, National Eye Institute.

BACKGROUND OF THE INVENTION

1. Field of the Invention

The present invention involves high numerical aperture (NA) lens assemblies. The present invention also involves a variable focus lens assembly including a first lens group and a second lens group, wherein a distance between the first lens group and the second lens group is adjustable to focus the variable focus lens assembly. The present invention may be used for examining body tissues, e.g., the cornea and the crystalline lens, at high NA such as at least about 0.65.

2. Discussion of Background

The cornea is a transparent tissue that not only allows transmission of light into the eye, but also provides most of the optical power for focusing images on the retina, the image sensing portion of the eye. Examination and treatment of the cornea is important because the regrowth of nerves after photorefractive keratectomy (PRK) and laser in situ keratectomy (LASIK) procedures is of interest in both research and clinical practice. Other procedures of more experimental nature can benefit from studies on the changes that are produced in nerve distribution, keratocyte density, haze, and epithelial cell regrowth (thickness and cell morphology).

The cornea is the most accessible component of the eye, and it has been studied extensively with microscopes of moderate and high resolution. In the living eye, the natural and frequent involuntary motions of the eye make it difficult to see and photograph fine details at high magnification. By the time the examiner identifies an image to be recorded, the eye may have moved in any or all of three dimensions. This problem is eased, but not completely solved, by having a distal end of the microscope objective suitably designed to contact the cornea, as disclosed in U.S. Pat. No. 5,359,373 to KOESTER et al. (hereinafter "KOESTER '373"), the disclosure of which is herein incorporated by reference in its entirety. The contact lens element serves to maintain the focus of the microscope at the same depth in the cornea, even when the eye rotates involuntarily. An additional advantage of contacting the cornea is that it establishes a plane of reference so that the depth of a region of interest can be determined by the setting of the microscope focus.

Another reason why the examination or treatment of the cornea is difficult is that the cornea is approximately 0.5 mm thick. In this regard, high numerical aperture (NA) objectives often have a limited range of high performance (diffraction limited) focal distance. For example, it is known that high NA objectives used to examine specimens on glass slides, with a cover glass between the specimen and the objective, can be used only with cover glasses having the thickness specified by the manufacturer. A few high NA objectives are made with a built-in adjustment that allows a small range of cover glass thicknesses to be utilized. Regarding examination and treatment of the cornea, high NA objectives tend to be diffraction limited over a limited range of about 0.1 mm of the cornea. Therefore, a lens assembly that is to have clinical application in examining or treating the cornea would preferably be able to obtain a sharp image over a substantial range of the thickness of the cornea.

Still another source of difficulty in examining or treating the cornea exists when the objects of interest lie at different depths in the cornea. In this regard, spherical and chromatic aberrations are generated at the interface between air and any medium having an index of refraction greater than 1.0. The magnitude of the spherical and chromatic aberrations increases with the thickness of the medium between the object to be examined and the surface (e.g., with the thickness of the cornea).

The difficulties involved in examining or treating the cornea also affect the examination or treatment of portions of the eye which are behind the cornea. For instance, the crystalline lens is located in humans approximately 4 mm behind the cornea. The crystalline lens provides additional optical power needed to focus the image precisely on the retina. In the crystalline lens, structures of interest include epithelial cells located close to the anterior and posterior surfaces of the lens, fibers within the interior of the lens, and suture lines where fibers from adjacent regions of the lens meet.

One reason why examination or treatment of the crystalline lens is difficult is that the position of the human crystalline lens varies from person to person. The position of the crystalline lens is defined by the anterior chamber (AC) depth and varies in the adult population over a range of at least 2.3 to 4.1 mm. BARRETT et al., *Optom. Vis. Sci.*, Vol. 73, pp. 482–86 (1996), the disclosure of which is herein incorporated by reference in its entirety. During an examination or treatment of the crystalline lens, it is important to be able to focus at various depths in order to locate the structures of interest, and to determine the relative longitudinal positions of various structures. Further, because of this variety in depth of the crystalline lens, if the crystalline lens is examined by directly contacting the corneal surface with an objective lens surface, an objective system that is useful for one patient may need to be changed when a patient with a different crystalline lens depth is to be examined. It would be desirable if a large percentage of the adult population could be examined with one objective lens system, rather than having to change the objective lens system for nearly every patient. Therefore, an objective lens system that is to have clinical application in examining or treating the crystalline lens would preferably be able to obtain a sharp image over a substantial range of AC depths.

Another difficulty in examining or treating the regions in the eye posterior to the cornea, such as the crystalline lens and iris, results from the cornea being aspheric to the extent that the curvature of the cornea is greatest at the center and less toward the periphery. Most corneas also have some astigmatism, i.e., greater curvature in one azimuthal direction than in the perpendicular direction. The irregular shape of the cornea affects the path of light through the eye. This aberration in the light path may be corrected by spectacles or contact lenses.

Further, almost all corneas, when measured carefully, have some degree of irregular astigmatism. In irregular astigmatism, irregularities in the shape of the cornea cannot be fully corrected by spectacles.

To correct corneal astigmatism, a rigid, i.e., non-flexible, contact lens may be utilized, since it will generally have a layer of tears between the lens and the cornea, the thickness of which will vary from center to edge. The layer of tears improves the image which reaches the retina because the refractive index of the tears (1.336) is closer to the refractive index of the cornea (1.376) than the refractive index of air (1.0). Thus, when a rigid contact lens is used, variations in cornea topography have less effect on light rays than they would when the cornea is in air. As a result, the optical effects of corneal irregularity are significantly reduced. However, if the cornea astigmatism is sufficiently large, there will be residual astigmatism due in part to the fact that the refractive index of the tear layer does not exactly match that of the cornea. Further, there may be astigmatism in the crystalline lens or other irregularity in the crystalline lens.

As a result, for many years, rigid contact lenses have been used with patients having irregular corneas, particularly corneas having high levels of astigmatism. A rigid contact lens with a spherical back surface is prescribed, and the tear layer between the back surface and the cornea reduces the aberrations of the cornea by a factor of about:

$$\frac{n_{cornea} - n_{tears}}{n_{cornea} - n_{air}} = \frac{1.376 - 1.336}{1.376 - 1.0} = \frac{0.040}{0.376} = 0.106$$

That is, the aberrating effect of an irregular cornea is reduced to about 10% of that for the cornea in air.

Taking into consideration the known methods for correcting vision, there are several known techniques for facilitating the examination or treatment of the eye. Biomicroscopes, also known as slit lamps, are often used with a diagnostic contact lens which is hand-held against the cornea, utilizing a viscous liquid such as a methylcellulose solution to form an optical coupling to the cornea.

The use of diagnostic contact lenses reduces the aberrations that would be produced by the same cornea in air. The layer of methylcellulose solution reduces the effects of astigmatism because the refractive index of the methylcellulose solution (1.337) is closer to the refractive index of the cornea (1.376) than the refractive index of air (1.0). As a result, variations in cornea topography have less effect on light rays than they would when the cornea is in air.

Examples of diagnostic contact lenses which are used in conjunction with biomicroscopes include diagnostic contact lenses made by Ocular Instruments, Inc. and Volk Optical Co. These contact lenses are hand-held lenses with concave front surfaces to contact the cornea, generally used with a viscous liquid such as methylcellulose solution. Some of these lenses are gonio-lenses which include inclined mirror surfaces that allow examination of various regions of the retina and the region called the angle of the anterior chamber. FIG. 5 of WILENSKY, "Optics of Gonioscopy", *Clinical Ophthalmology*, Vol. 1 (1990), the disclosure of which is herein incorporated by reference in its entirety, shows how the gonio-lenses contact the eye, and how a ray of light travels from the angle recess of the eye to the mirror surface and then out of the lens.

KOESTER '373, which is briefly discussed above, involves a contact lens element that is moved relative to a high NA objective during focusing. Such objectives have been found to be valuable for studying cell structure, nerve configurations and the growth of nerves in the cornea, and identification of certain types of corneal diseases.

Microscope objective lenses with high NA are required for these applications since the resolution of the microscope increases in proportion to the NA of the objective. As noted above, in most objective lenses having high NA, the resolution is optimum over a very narrow range of focal distances. The apparatus of KOESTER '373 has an acceptable range of focus of about ±0.1 mm. In order to cover the 0.5 mm thickness of cornea, it is necessary to fabricate several contact lens elements to provide acceptable images over this range of focal depth.

KOESTER '373 discloses a contact lens element with a flat front surface for contacting the cornea to stabilize the longitudinal position of the cornea. Because the contact lens element flattens the portion of the cornea against which it is pressed, the contact lens element helps to reduce aberrations caused by the normal, unflattened shape of the cornea. KOESTER '373 discloses that small variations from flatness can be utilized, and discloses that if the surface is concave with a radius of curvature less than that of the cornea, it is possible to trap air bubbles in the tear layer between the contact lens element and the cornea, thereby disrupting the optical continuity of the system. KOESTER '373 also indicates that while a concave contact surface might have optical advantages, it could possibly cause a greater distortion of the cornea if it is not precisely aligned with the axis of the cornea.

The flat contact lens element of KOESTER '373, while useful for examining the cornea, is not suitable for examination of the crystalline lens and details at other depths within the eye. The flattening of the cornea has the effect of causing wrinkles, which show up as a corneal mosaic as discussed in AURAN et al., "Wide Field Scanning Slit in Vivo Confocal Microscopy of Flattening-Induced Corneal Bands and Ridges", *Scanning*, Vol. 16, pp. 182–86 (1994), the disclosure of which is herein incorporated by reference in its entirety. These wrinkles produce inhomogeneities in the optical path through the cornea and have been observed to result in a blurring of the retinal image during examination at high magnification.

KOESTER et al., "Clinical Microscopy of the Cornea Utilizing Optical Sectioning and a High-Numerical-Aperture Objective", *J. Opt. Soc. Am. A*, Vol. 10, No. 7 (July 1993), the disclosure of which is herein incorporated by reference in its entirety, discloses contact lens elements similar to those disclosed in KOESTER '373. This article discloses that a slightly concave surface can be used for the contact lens element, as long as the radius of curvature is greater than that of the cornea, to reduce the possibility of trapping air bubbles between the contact lens element and the cornea.

In the examination of the cornea, the Tomey confocal microscope is finding good acceptance. The Tandem Scanning confocal system is now being offered by Advanced Scanning Limited, New Orleans, La. The Tandem Scanning confocal system, which has a NA of about 0.60, involves a lens having positive optical power designed to contact the cornea and an internal lens which moves relative to the lens in contact with the cornea. The Tandem Scanning confocal system, however, is designed to investigate the cornea.

U.S. Pat. No. 4,666,456 to SHIMIZU et al., the disclosure of which is herein incorporated by reference in its entirety, discloses a construction involving three lens groups in which the middle lens group is moved along the optical axis to correct deterioration of image performance due to various thicknesses of parallel glass plates, e.g., microscope cover glasses. The first lens group has positive refractive power while the second and third lens groups have negative refractive power. The function of the second lens group is also to create negative spherical aberration of variable magnitude.

U.S. Pat. No. 576,896 to RUDOLPH, the disclosure of which is herein incorporated by reference in its entirety, discloses that two glasses having similar indices of refraction and different dispersions may be used to correct chromatic aberrations.

KINGSLAKE, *Lens Design Fundamentals*, pp. 105–07 (1978), the disclosure of which is herein incorporated by reference in its entirety, shows that in certain lens systems, as the focal distance is increased, spherical aberration passes through a zero point, increases slowly and reaches a maximum point. KINGSLAKE also discloses a maximum positive value of spherical aberration when the radius R is about:

$$R=1.2*r_{apl} \quad \text{(eq. 1)}$$

where $r_{apl}$=the aplanatic radius for the particular index of the glass:

$$r_{apl}=L/(1+n) \quad \text{(eq. 2)}$$

where n=index of refraction of the glass, and L=the distance from the surface to the point of convergence of a bundle of rays entering the surface.

With the above in mind, there exists a need for a high NA lens assembly which is diffraction limited and which can focus over a broad range. For instance, such a lens assembly could be used to examine or treat transparent or semi-transparent materials including body tissues such as the cornea or the crystalline lens.

SUMMARY OF THE INVENTION

It is an object of the present invention to provide a variable focus, high numerical aperture (NA) lens assembly which is diffraction limited.

It is an object of the present invention to examine or treat transparent or semi-transparent materials, such as body tissues, at high NA.

It is another object of the present invention to provide a variable focus lens assembly which contacts the cornea, to stabilize the position of the eye relative to the objective of the variable focus lens assembly.

It is another object of the present invention to provide a variable focus lens assembly having an internal focusing adjustment, so that a contact lens element contacting the cornea is not moved during focusing.

It is another object of the present invention to provide objective lenses for examining the cornea at high NA.

It is still another object of the present invention to provide a high magnification, high resolution microscope objective that contacts the cornea and can be focused at any depth within the 0.5 mm thickness of the cornea.

It is yet another object of the present invention to be able to focus at greater depths in edematous (swollen) corneas, particularly when utilized with a confocal microscope.

It is still another object of the present invention to provide objective lenses for examining or treating the crystalline lens, such as the anterior and posterior poles of the crystalline lens, at high NA.

It is another object of the present invention to provide a variable focus lens assembly with a contact surface that minimizes distortion of the cornea.

It is another object of the present invention to provide a variable focus lens assembly which is useful in laser treatment or other focused radiation treatments such as photodynamic therapy.

It is yet another object of the present invention to examine or treat tissues other than the cornea and the crystalline lens, such as skin, lesions of the skin, other tissues that are naturally exposed or are exposed by surgery.

In accordance with one aspect, the present invention is directed to a variable focus lens assembly, comprising: a first lens group with positive optical power; a second lens group with positive optical power; an adjuster structured to be capable of adjusting a separation between the first lens group and the second lens group; and wherein the variable focus lens assembly has a numerical aperture greater than about 0.65.

In accordance with another aspect, the present invention is directed to a variable focus lens assembly, comprising: a first lens group that is moveable on an axis, the first lens group being well-corrected and having a numerical aperture of at least about 0.20; a second, fixed lens group sharing the axis of the first lens group; wherein a distance between the first lens group and the second lens group may be varied over a range; wherein the variable focus lens assembly has a spot size which is diffraction limited over the range of distance separating the first lens group and the second lens group; and wherein the variable focus lens assembly has a numerical aperture of at least about 0.65.

In accordance with still another aspect, the present invention is directed to a variable focus lens assembly, comprising: a first lens group; a second lens group associated with the first lens group, the second lens group comprising a first surface having a convex radius r; wherein a distance between the first lens group and the second lens group may be varied over a range; and wherein the association between the first lens group and the second lens group is such that converging light from the first lens group is focused toward a point at an adjustable distance L inside the first surface of the second lens group, and the ratio L/r is about 1.57 to 2.52 at some point in a range of adjustment of the first lens group relative to the second lens group.

In accordance with yet another aspect, the present invention is directed to a method for examination or treatment of the eye, comprising: providing a system comprising a contact lens element having a recess capable of holding a volume of liquid against a cornea of an eye to be examined or treated, and a microscope unit adjustably connected to the contact lens element; placing the contact lens element on the cornea to form a substantially enclosed space between the contact lens element and the cornea; at least one of filling the substantially enclosed space with liquid and allowing the substantially enclosed space to become filled with liquid; and adjusting the position of the microscope unit to focus an image while the contact lens element remains substantially stationary against the cornea.

In one aspect, the first lens group comprises a microscope objective having a working distance greater than about 5 mm.

In another aspect, the second lens group is immersed to an object with a fluid having an index of refraction greater than about 1.33.

In still another aspect, the adjuster is structured to be capable of adjusting the first lens group along an axis of the first lens group and the second lens group in order to focus the variable focus lens assembly.

In yet another aspect, the second lens component comprises: a first lens component having a surface for contacting air, the surface producing chromatic aberration; a second lens component associated with the first lens component; a third lens component which is cemented along a spherical surface to the second lens component; and wherein the second lens component and the third lens component comprise materials which have indices of refraction which differ by less than about 0.005 and have Abbe v numbers that differ by more than about 10. The materials of the second lens component and third lens component may have indices of refraction which differ by less than about 0.003 and have Abbe v numbers that differ by more than about 12. Further, the two lens components of the second lens group may have indices of refraction that differ by no more than about 0.0025 and have Abbe v numbers that differ by at least about 22.

In yet another aspect, a proximal surface of the second lens group comprises a radius such that light from the first lens group is incident so that spherical aberration of the proximal surface has a slope relative to focal distance which is less than a slope of spherical aberration relative to focal distance at an aplanatic point, over the range of distance separating the first lens group and the second lens group.

In still another aspect, the spherical aberration is near a local maximum overcorrection condition over the range of distance separating the first lens group and the second lens group.

In another aspect, a distal surface of the second lens group comprises a circular rim for contacting a cornea of an eye to be examined or treated, the diameter of the circular rim being about 6 to 11 mm. Similarly, a distal surface of the second lens group may comprises a concave surface having a radius of curvature which is less than that of a cornea of an eye to be examined or treated.

In a further aspect, a distal surface of the second lens group comprises one of a flat surface and a convex surface having a radius of curvature which is greater than about 5 mm.

In still another aspect, the first lens group and the second lens group comprise a portion of a confocal microscope.

In another aspect, the second lens group is capable of holding a liquid against a cornea of an eye to be examined or treated, the liquid being an optically clear liquid having a refractive index of about 1.33 to 1.42.

In another aspect, the circular rim comprises a diameter which is greater than a diameter of a light beam passing through a surface of the cornea.

In another aspect, the microscope unit comprises a microscope comprising an external lens, and a lens rigidly connected to the external lens of the microscope.

In another aspect, the microscope unit comprises a microscope objective.

In another aspect, the method comprises contacting a distal end of the second lens group of the variable lens assembly with an object to be examined; and examining the object.

In one aspect, the method comprises focusing on a region within the eye.

In another aspect, the method comprises providing a variable focus lens assembly, wherein the second lens group comprises a circular rim; contacting the cornea of the eye with the circular rim of the second lens group; and one of examining and treating the region within the eye.

In yet another aspect, the method comprises providing a variable focus lens assembly, wherein the second lens group comprises a distal surface; contacting the distal surface of the second lens group with the body tissue; and one of examining and treating the body tissue.

In another aspect, the method comprises examination of one of surface detail and subsurface detail of the body tissue.

In another aspect, during the method, the contact lens element maintains the eye in substantially the same longitudinal position.

BRIEF DESCRIPTION OF THE DRAWINGS

The present invention is further described in the detailed description which follows, in reference to the noted plurality of non-limiting drawings, wherein.

DESCRIPTION OF THE INVENTION

Figure 1:
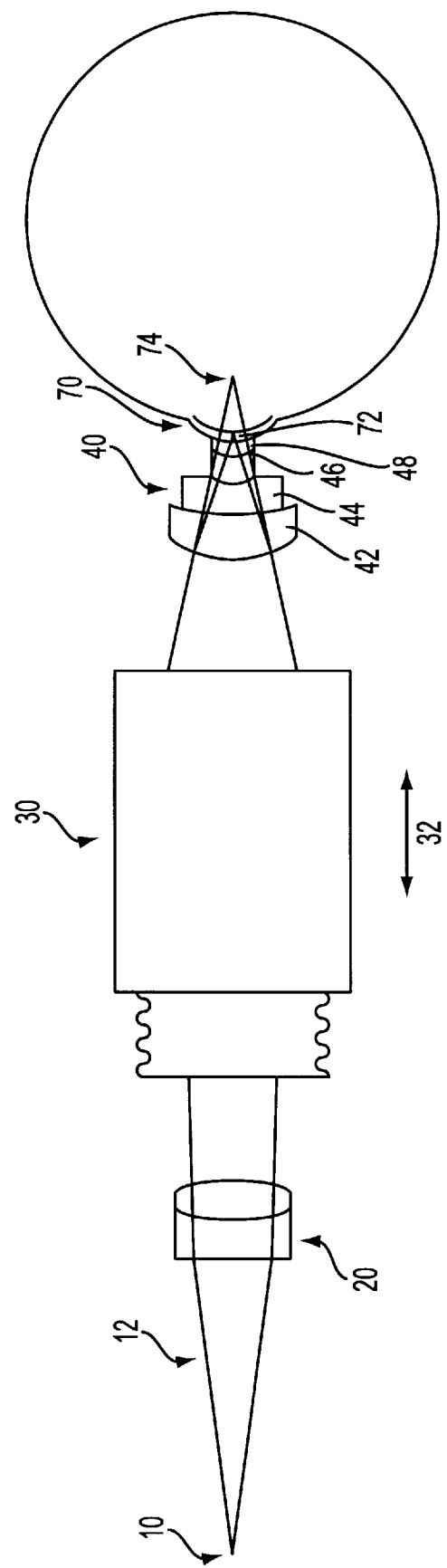
FIG. 1 is a schematic illustrating a variable focus lens assembly for examining the cornea of the eye.

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description taken with the drawings making apparent to those skilled in the art how the several forms of the invention may be embodied in practice.

As a preliminary matter, it is noted that when an image is formed in a microscope, light travels from the object point through the objective lens and is focused at the image plane. However, it is easier to explain and understand the operation of the invention in terms of light traveling from the image plane of the microscope to the object plane (the latter is often referred to as the focal plane of the microscope system). A universal principle in lens optics is that if light travels from left to right along a certain path, then it can also travel from right to left along exactly the same path.

Unless otherwise stated, all refractive indices are measured with light having a wavelength of 587.6 nm.

Before further discussion, a definition of the following terms will aid in the understanding of the present invention:

MICROSCOPE: device comprising an objective lens and at least one of an eye piece lens and an image capturing device such as photographic film or a charge coupling device (CCD) camera.

NUMERICAL APERTURE (NA): a measure of the power of a microscope objective, equal to the product of the refractive index of the medium at the front focal plane of the objective and the sine of the angle between the optical axis and outermost ray in the medium at the focal plane.

SACCADE: a rapid intermittent eye movement, as one that occurs when the eye fixates on one point after another in the visual field.

RADIUS OF CURVATURE OF CORNEA: radius of curvature as measured at the center portion of the cornea where the center portion has a diameter of 3 mm.

DISPERSION: difference in index of refraction of a material at two different wavelengths. One measure of dispersion is the Abbe ν number=$(n_D-1)/(n_F-n_C)$, where $n_D$, $n_F$, and $n_C$ indicate indices of refraction at the wavelengths 587.6 nm, 486.1 nm, and 656.3 nm, respectively.

DIFFRACTION: the bending of light rays as they pass by an obstruction or through an opening such as the aperture of a lens.

AIRY DISC: the image point of a point source produced by a perfect optical system having a circular aperture. This image has a bright central disc, surrounded by dark rings and light rings of decreasing intensity.

RADIUS OF AIRY DISC: the radius of the first dark ring of the Airy disc.

DIFFRACTION LIMITED: this term indicates that the image quality is limited primarily by diffraction of light as it passes through the optical elements and apertures, and is not limited by spherical, chromatic, or other aberrations. Thus, the image of the point source is an Airy disc, the size of which is dictated by diffraction, not by any aberrations in a lens.

WELL-CORRECTED LENS: lens which has diffraction limited performance on axis and which has substantially diffraction limited performance over the full field of the lens. Thus, a well-corrected lens is corrected for spherical aberrations, chromatic aberrations, and curvature of field.

ROOT MEAN SQUARE (RMS) VALUE: the square root of the average of the squares of a series of related values.

OPTICAL PATH DIFFERENCE (OPD): the difference in optical path between two light rays passing from the object to the image along two different paths.

ROOT MEAN SQUARE VALUE OF THE OPTICAL PATH DIFFERENCE (RMS OPD): square root of the average of squares of the OPD values for an appropriate sampling of the rays forming the image of a point source.

SPOT DIAGRAM: shows the locations in the image plane of rays from a point source, as calculated by ray tracing. A perfect optical system would produce only one point of intersection, i.e., all rays imaging at one focal point. For all practical lenses, the spot diagram has a distribution of points.

RMS RADIUS OF THE SPOT DIAGRAM: root mean square of the distance from the center of the spot diagram to each point.

As an overview, the present invention is directed to a lens assembly including a combination of at least two lenses in which the separation between the lenses can be varied in order to control the focal length and the image distance. The first lens is aligned with the axis of the second lens, with the first lens being adjustable in longitudinal position until the focal point of the combination is at the desired distance from the second lens. The first lens may be a microscope objective having a long working distance. The second lens may have a surface which has positive spherical aberration that is substantially constant or varies slowly as the distance between the first and second lenses is varied. Both the first and second lenses may have positive optical power. It is important to note that the design of the second lens is expeditiously optimized by computer.

The present invention may be used to examine transparent and semi-transparent materials including body tissues such as the eye. When used to examine the eye in vivo, the second lens may be placed in contact with the cornea to stabilize the position of the eye. The optical system, including the lens assembly and the eye, preferably has net spherical aberration and chromatic aberrations that are minimal, so that the image is diffraction limited on axis. In view of the above, the present invention may be used to examine cells, nerves, and other details in the cornea, as well as cells, fibers and other structures in the crystalline lens. The present invention may also be used in other microscope applications such as fluorescence microscopy and tissue culture examination. Further, the present invention may be used in confocal microscopes for examining the eye. With modifications in the design, the present invention may also be used to examine other accessible tissues, including skin and conjunctiva.

It has been discovered that the following procedures may be advantageously used to obtain variable focus lens systems having high numerical aperture (NA) and extended focal range. The design procedure, which is discussed in more detail below, involves:

(1) Select a long working distance objective lens with as high an NA as is available.

(2) Begin the design of the second lens group by selecting a first lens component and a radius of curvature for the first surface that will produce the desired NA and will generate the desired level and slope of positive (overcorrected) spherical aberration, as described in the examples given in the specific design discussions below.

(3) Select lens second and third components that have equal or nearly equal indices of refraction, but widely different dispersions. Choose the radius of the cemented surface between these glasses so that the chromatic aberration created by this surface is equal and opposite to that created by the first surface (in the center of the range of focus).

(4) Add a fourth lens component, if needed, to interface with the object, such as the cornea of the eye.

(5) Utilize optical design software with the capability to optimize multiple configurations. First optimize the system for one configuration, in which the focal point is at or near the center of the range of desired focal planes. The optimization criteria should include the desired NA, the desired image quality, and any other constraints such as size of the elements, location of the image, etc. The variables may include radii, thicknesses, and glass indices (and dispersions) for each of the lens components.

(6) Set up a second configuration that differs only in that it has a focal point that is separated from the first focal point of (5) by a short distance along the axis. That distance could be, for example, 5 to 10% of the total range of focus that is desired for the system.

(7) Repeat (6) by moving the focal point of the first configuration a short distance in the opposite direction, and repeating the optimization. Continue this iteration until the desired image quality is achieved over the required range of focal depth, at the desired NA.

Referring to the drawings, FIG. 1 is a schematic showing components of a lens assembly which is being used to examine a cornea 70. The components of the lens assembly include a lens 20, an objective 30, and a contact lens element 40.

The normal image position is at 10, but for purposes of explanation the source of rays 12 is considered to be at point 10, from which the rays 12 travel to the right through lens 20. Lens 20, which has positive optical power, is a tube length corrector, which causes the image of point 10 to appear at the distance from objective 30 for which this objective lens is designed.

After passing through lens 20, the light passes through objective lens 30. The objective lens 30 has a positive power, and is preferably a well-corrected, high numerical aperture (NA), very long distance microscope objective. Taking into consideration that high NA is desirable in the present invention, the NA of the objective 30 is preferably at least about 0.20, more preferably at least about 0.35, and most preferably at least about 0.40, with a range such as about 0.20 to 0.40. Taking into consideration that long working distance is desirable in the present invention, the working distance is preferably at least about 10 mm, more preferably at least about 12 mm, most preferably at least about 20 mm, with a range such as about 10 mm to 25 mm. For instance, the objective 30 may have an NA of 0.40 and a magnification of 20X, such as an Olympus or Nikon long working distance microscope objective.

The light rays leaving the objective 30 are directed toward point 74, where they would come to a focus if there were no other optical elements in the path. The contact lens element 40, however, refracts the rays so that after passing through the cornea the light focuses in the cornea 70 at a focal point 72, as shown more clearly in FIG. 3. As a result, the variable focus lens assembly of the present invention preferably has a relatively high NA, such as preferably at least about 0.35, more preferably at least about 0.65, most preferably at least about 0.80, with ranges of preferably about 0.65 to 0.75, more preferably about 0.78 to 0.82.

Although the focal point 72 is shown to be at the cornea 70 in FIG. 1, the optical system may be modified to examine other portions of the eye such as the crystalline lens. Furthermore, the present invention may be used for examining other transparent or semi-transparent materials such as tissues which include skin (to a depth limited only by the scattering properties of the tissue), organs that can be accessed by surgery or by endoscopy, and thick tissue mounts in biological experiments.

The contact lens element 40 may be in accordance with U.S. application Ser. No. 09/074,402 or U.S. Provisional Application No. 60/084,789, the disclosures of which are herein incorporated by reference in their entireties. Further, the contact lens element 40 may have features as discussed below.

The contact lens element is preferably physically mounted on the microscope objective. Depending upon the sensitivity of the contact lens element, however, the contact lens element of the present invention may be hand-held against the cornea, and any viewing instrument may be used to examine the eye by viewing through the contact lens element of the present invention. However, attaching the contact lens element of the present invention to a microscope is desirable so that the contact lens element and the microscope remain in alignment. Thus, physical attachment of the contact lens element 40 to the microscope objective 30 facilitates accurate alignment of the contact lens element 40 with respect to the optical axis of the rest of the optical system of the microscope.

Figure 2:
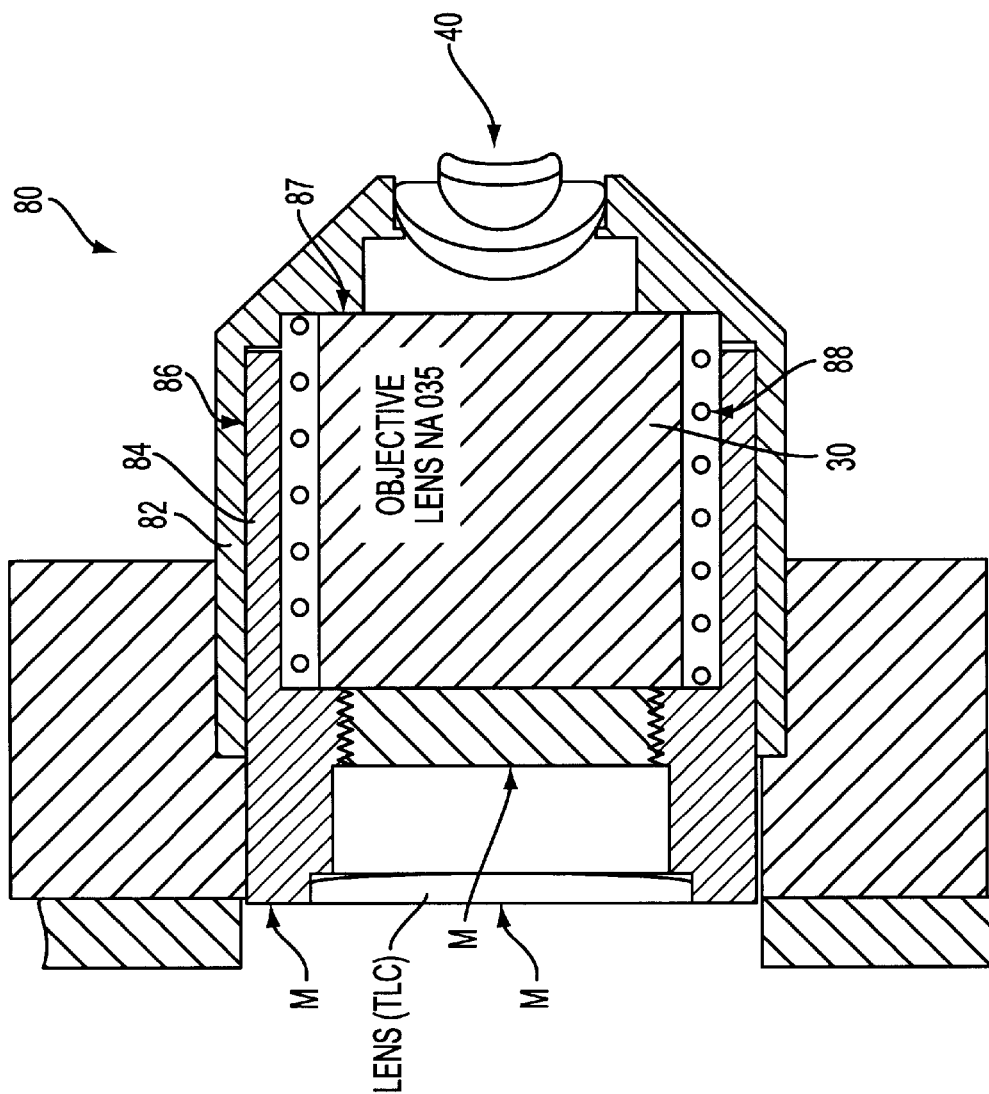
FIG. 2 is a schematic illustrating the mounting of the variable focus lens assembly of FIG. 1.

FIG. 2 illustrates a mount 80 for mounting and focusing the variable focus lens assembly. Mounting is important because it facilitates aligning and centering of the optics, including the eye.

The mount 80 includes a sleeve bearing mount 82. Within the sleeve bearing mount 82 is an inner bearing mount 84 which is attached to the objective 30. The inner bearing mount 84 includes a bearing surface 86 adjacent to the sleeve bearing mount 82. The inner bearing mount 84 is capable of sliding motion as illustrated by each direction of Arrow 32, with moving parts being labelled M. In this regard, the objective is shown in a stop position at the right of FIG. 2 in which the objective 30 contacts a stop surface 87 of sleeve bearing mount 82. In this embodiment, a compression spring 88 biases the objective 30 to the left as shown in FIG. 2.

The purpose of the sliding motion is to adjust the distance between the objective 30 and the contact lens element 40 to focus the image and to adjust the focal depth. The relative position of the sleeve bearing mount 82 and the inner bearing mount 84 may be adjusted by various adjustment mechanisms (not shown).

Focusing the image and changing the focal depth are accomplished by use of a fine focus mechanism of the microscope. In this regard, the sleeve bearing mount 84 is connected to a fine focus mechanism of the microscope.

Figure 3:
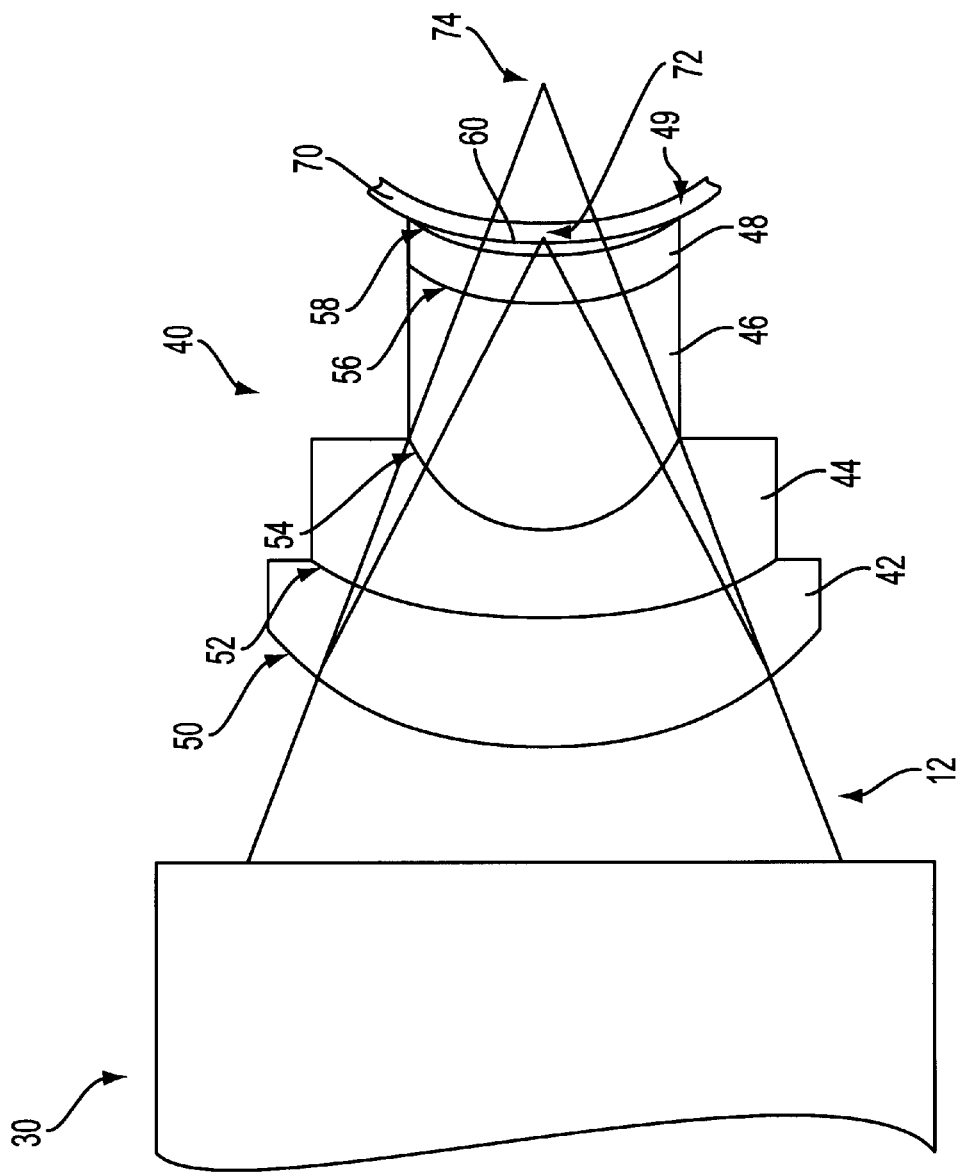
FIG. 3 is an enlarged view of a portion of FIG. 1 which involves the contact lens element.

Referring to FIGS. 1–3, the contact lens element 40 has positive optical power. The contact lens element may be a multi-component assembly which may be cemented together or separately mounted. The embodiment shown in FIGS. 1–3 includes four lens components 42, 44, 46, and 48, which form surfaces 50, 52, 54, 56, and 58. Although the contact lens element 40 of FIGS. 1–3 includes four lens components, the contact lens element of the present invention may include one or more lens components. If only one lens component is used, the contact lens element does not have the same focus for light of different wavelengths, e.g., red and blue, and chromatic aberrations result. Further, if only one lens component is used, the contact lens element does not have the same focus for light passing through the center of the lens and for light passing through outer portions of the lens, i.e., spherical aberrations in which all light rays do not come to the same focal point.

Accordingly, the contact lens element of the present invention preferably includes more than one lens component to correct for lens aberrations such as chromatic and spherical aberrations. As discussed below, the chromatic and spherical aberrations may be corrected by known techniques involving using lens components that are made of different, transparent materials having substantially different dispersions, i.e., large differences in the rate at which the index of refraction changes with wavelength. Thus, as described in more detail below, the contact lens element 40 is designed to (1) increase the NA of the system; (2) produce a diffraction limited image with the objective 30; and (3) maintain the diffraction limited image quality over an extended range of focal depth.

The contact lens element 40 is held essentially stationary in contact with the cornea 70. In the examination of human eyes, in vivo, it is advantageous to have the contact lens element 40 contact the cornea 70 to stabilize the eye. The contact does not stop the eye from rotating, which the eye does involuntarily quite frequently, in short sudden movements. But the contact does stabilize the longitudinal position of the eye, thus keeping the focal plane at a particular depth in the eye.

As explained in U.S. application Ser. No. 09/074,402 and U.S. Provisional Application No. 60/084,789, there is further advantage if the contact with the cornea is along a circular rim 49 that is larger in diameter than the area through which the light beam is passing. The contact is along the rim 49 of the contact lens element 40 because lens surface 58 has a radius of curvature slightly less than that of the cornea 70. The radius of curvature of surface 58 is preferably less than about 8 mm, more preferably about 5.5 to 7.6 mm. When the radius of curvature of surface 58 is less than that of the cornea 70, a thin layer of tears 60 fills the space between the contact lens element 40 and the cornea 70.

In the design of contact lens element 40, an important consideration is that objective lens 30 is mounted on a focus adjusting mechanism so that it can be moved in the direction shown by Arrow 32. As the objective 30 moves to the right, for example, the objective 30 will shift the position of the focus to the right. While this action is expected for any type of lens in the position of the contact lens element 40, a feature of the invention is that the image will remain at high resolution over a broad range of focal distance. The range of diffraction limited focal distance is preferably at least about 0.5 mm, more preferably at least about 0.6 mm, and most preferably at least about 0.7 mm, with a range of preferably about 0.5 to 0.7 mm when the contact lens element is designed to examine the cornea, and with a range of preferably about 0.8 to 1.3 mm when the contact lens element is designed to examine regions of the eye behind the cornea.

The contact lens element 40 increases the NA of the system by increasing the convergence of the rays. A first surface 50 of contact lens element 40 is designed to do most of the bending of the rays, to produce the desired NA. As discussed in more detail below, the radius of curvature of surface 50 depends on the working distance of the objective, the depth of the focal plane, and the specific design of the contact lens element.

Surface 50 will normally produce significant spherical and chromatic aberration. Furthermore, the magnitude of these aberrations will change as objective lens 30 moves toward or away from contact lens element 40. However, as discussed below, it is possible to achieve a configuration in which the spherical aberration due to surface 50 is balanced out by spherical aberration from other surfaces.

Thus, the first surface 50 of the contact lens element 40 is selected by choosing the lens component composition and the radius of curvature so that two conditions are substantially satisfied:

(1) Rays converging from the first lens group are preferably refracted to produce the desired NA in the object space. While the final NA cannot be determined until the design is complete, the first surface 50 generally produces most of the increase in NA in this design.

(2) The radius of curvature of the first surface 50 is preferably selected so that over the range of focus the spherical aberration is positive in sign and changes slowly with the change in focal depth.

With the above in mind, examples of the radius of curvature of surface 50 range from at least about 7 mm to 10 mm.

Figure 4:
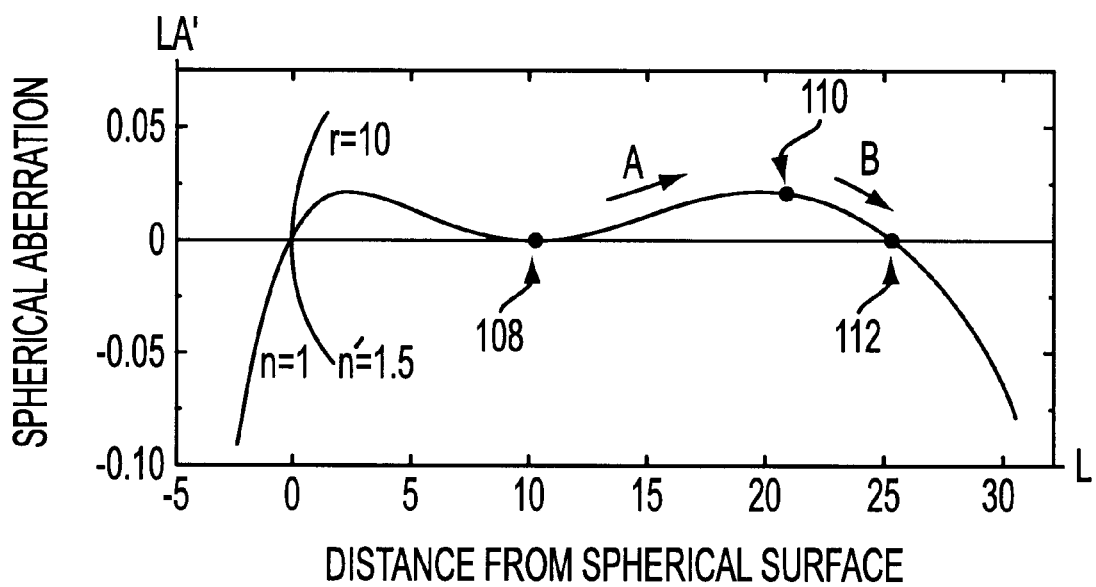
FIG. 4 is a graph showing a range of focus in which spherical aberration is predominantly positive in sign and changes slowly with changes in focal depth.

Regarding the goal of ensuring that over the range of focus the spherical aberration is positive in sign and changes slowly with the change in focal depth, the present invention relies upon a principle which is illustrated in FIG. 4, which is similar to FIG. 56 of KINGSLAKE, *Lens Design Fundamentals*, (1978), the disclosure of which is herein incorporated by reference in its entirety. As shown in FIG. 4, as the focal distance is increased, i.e., moves from left to right on the curve of FIG. 4, spherical aberration passes through a zero point 108, increases slowly (as shown by Arrow A) and reaches a local maximum at point 110. After reaching the local maximum 110, the spherical aberration then decreases slowly (as shown by Arrow B) at first, then crosses the X-axis at point 112. Point 112 is designated the aplanatic point. In view of the above, the relatively more desirable portion of the spherical aberration curve is that portion where the slope of the spherical aberration curve is less than the slope of the spherical aberration curve at the aplanatic point, more preferably less than about 50% of the slope of the spherical aberration curve at the aplanatic point, and most preferably less than about 25% of the slope of the spherical aberration curve at the aplanatic point.

Figure 5:
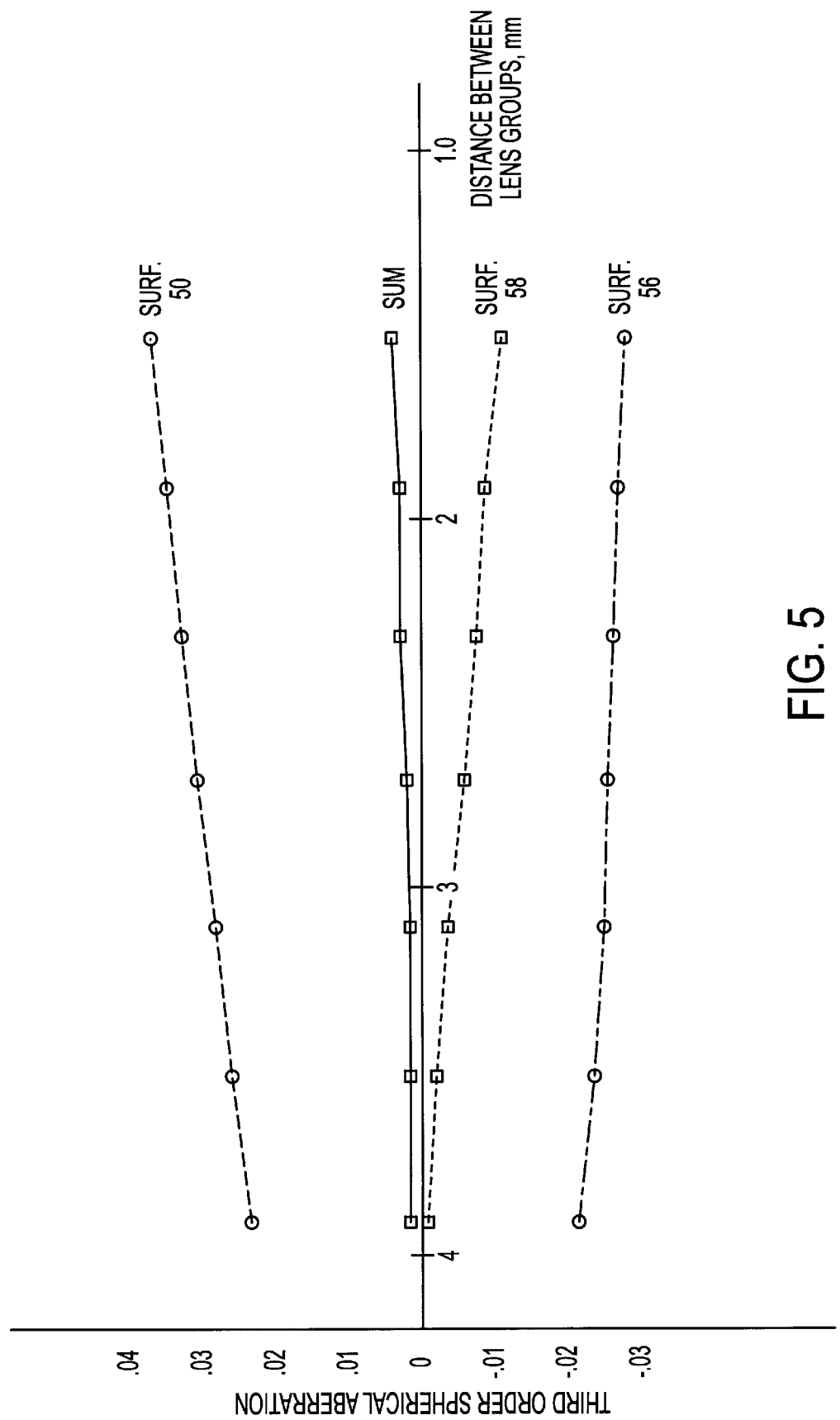
FIG. 5 is a graph showing variations in spherical aberration of several surfaces as the distance between lens groups is varied, and that the positive slope of one surface can be balanced by the negative slopes of other surfaces in order to minimize the net amount of spherical aberration.

To obtain the relationship shown in FIG. 4, the first surface 50 of the contact lens element 40 is designed to produce overcorrected spherical aberration. This situation is represented in FIG. 4 by the region of the curve between 108 and 112. This overcorrection then serves to compensate for the undercorrected spherical aberration produced by other spherical surfaces in the system, as illustrated in FIG. 5 which is discussed in more detail below. In a range of distance which separates the objective 30 and contact lens element 40, the spherical aberration may be:

(1) at or near a local maximum;
(2) between a zero point, such as 108, and a local maximum point, such as 110; and
(3) in a range from halfway between a zero point, such as 108, and a local maximum, such as 110, to halfway between a local maximum and an aplanatic point, such as 112.

Although the position on the curve of FIG. 4 may be at or near the local maximum 110, the preferred position on the curve of FIG. 4 for the variable focus system depends upon the object to be examined. For instance, when the eye is examined, the two surfaces of the cornea produce undercorrected spherical aberration of a magnitude that can be corrected by adjusting the overcorrection of the first surface 50. In particular, for examination of the crystalline lens, it is often preferable for the variable focus lens system to be to the left of the local maximum 110 shown in FIG. 4.

The refraction at the first surface 50 of contact lens element 40 also produces chromatic aberration, in which rays of different wavelengths are refracted to a different extent, e.g., rays of blue light are refracted more strongly than the green and red rays. The first surface 50 will necessarily produce negative chromatic aberration, and its magnitude will increase as the distance between the contact lens element 40 and the objective 30 decreases. Dispersion is specified by the Abbe $\nu$ number, where $\nu=(n_D-1)/(n_F-n_C)$, and where $n_D$, $n_F$, and $n_C$ indicate indices of refraction at the wavelengths 587.6 nm, 486.1 nm, and 656.3 nm, respectively. In this definition, large values of $\nu$ indicate small dispersion and vice-versa. For this reason, the dispersion of the first lens component 42 is preferably low. In particular, the $\nu$ number of the first lens component 42 is preferably about 40 to 80, more preferably about 50 to 70, and most preferably about 56 to 60.

If the chromatic aberration produced by the first surface 50 is not corrected, it can lead to images that are blurred by the presence of a colored fringe around the image of any bright source, or a colored border along a dark edge. This aberration is usually corrected by utilizing two lens materials with different values of dispersion. A color-corrected doublet utilizes two such lens materials cemented together along a spherical surface. Such a cemented surface usually produces some degree of spherical aberration in addition to correcting the chromatic aberration.

In particular, a second surface 52 is a cemented surface and the second lens component 44 is chosen to have nearly the same index of refraction as that of the first lens component 42 but a greater dispersion. The difference in index of refraction between lens components 42 and 44 is preferably less than about 0.005, more preferably less than about 0.02, and most preferably less than about 0.01. The difference in $\nu$ values of dispersion between lens component 42 and lens component 44 is determined by the magnitude of the chromatic aberration introduced by surface 50 and other surfaces in the system. In the embodiment shown in FIGS. 1–3, the difference in $\nu$ number between lens component 42 and lens component 44 has been as low as about 12 and as high as about 26.

The radius of curvature of the second surface 52 is selected so that the surface 52 is approximately concentric with the converging rays from the first surface 50. This condition should be satisfied at or close to the center of the range of focal depth. With the above in mind, the radius of curvature of surface 52 is preferably about 13 to 14 mm in embodiments similar to that shown in FIGS. 1–3. Because the surface 52 is approximately concentric (i.e., concentric to the center of the infinite rays), the spherical and chromatic aberrations contributed by surface 52 will be zero or small throughout the range, depending on the choice of materials for lens components 42 and 44.

The chromatic aberration produced by surface 50 is compensated by surface 54. Surface 54 joins lens components 44 and 46, which have the same, or nearly the same, index of refraction at the central wavelength (587.6 nm). The difference in index of refraction between lens components 44 and 46 is preferably less than about 0.005, more preferably less than about 0.003, and most preferably less than about 0.0025.

In the embodiment of FIGS. 1–3, lens component 44 has a greater dispersion than does lens component 46. The difference in $\nu$ number is preferably at least about 10, more preferably at least about 12, even more preferably at least about 15, even more preferably at least about 22, and most preferably at least about 25.

The radius of curvature of surface 54 is expediently optimized and selected by the computer lens design program to produce the required amount of chromatic aberration to balance that produced by surface 50, and other surfaces in the system.

At a fourth surface 56, lens component 48 has an index of refraction and dispersion as close as possible to that of the cornea or other object which is contacted, e.g., a tear layer between the contact lens element and cornea. However, an exact match is not possible with available glass or rigid plastic materials.

Therefore, the aberrations that are generated at the interface between lens component 48 and the object ought to be balanced by those generated at surface 56, or by adjustments to the aberrations introduced at surfaces 50, 52, and 54.

Figure 6:
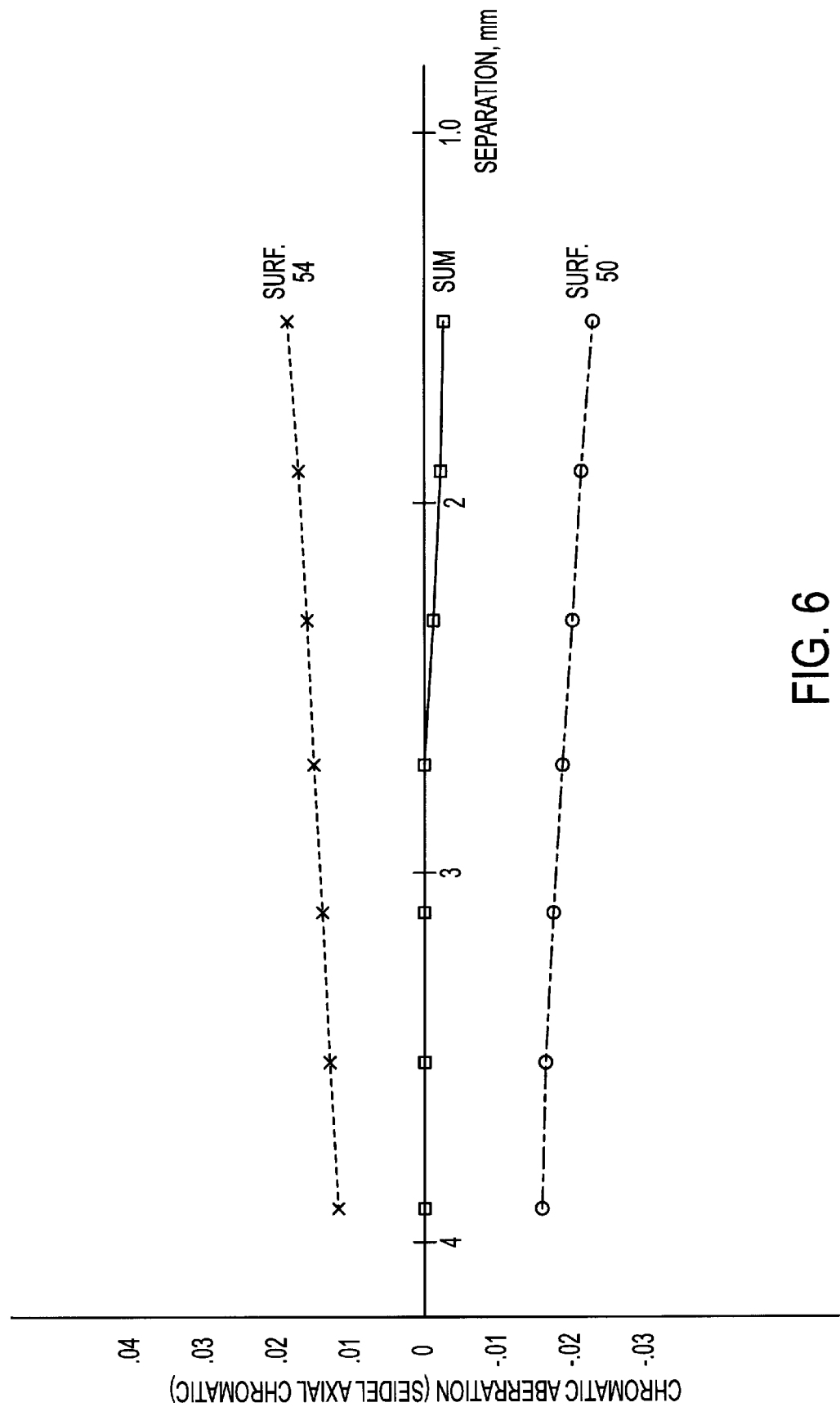
FIG. 6 is a graph showing that chromatic aberration may be balanced between lenses as the focal distance is varied in order to minimize the net amount of chromatic aberration.

The discussion so far indicates how the aberrations can be minimized, but only at one point in the range of focal depths. Surface 50 generates negative chromatic aberration that increases in magnitude as the separation between contact lens element 40 and the objective 30 is decreased, as illustrated in FIG. 6 which is discussed in more detail below. Surface 54 generates positive chromatic aberration that increases as the separation decreases, and therefore compensates for the effects of surface 50. The magnitude of the compensation depends on the radius of surface 54 and the difference in dispersion between the two lens components 44 and 46 and, therefore, provides a tool for the designer to provide compensation over the desired range of focal depth. The designer chooses dispersions for lens components 44 and 46, and the radius of surface 54 so that the compensation is as complete as possible over the desired range of focus. FIG. 6 illustrates that in the final design the positive chromatic aberration provided by surface 54 is nearly equal and opposite to that generated by surface 50, both in magnitude and slope. Other surfaces generate small amounts of chromatic aberration (not shown) so that the sum for all surfaces is not determined solely by surfaces 50 and 54 but the sum is very close to zero over the entire range.

A significant amount of spherical aberration is generated at surface 58, the interface between lens component 48 and the cornea 70. If the focal plane is at or near this interface at some point in the range, then the spherical aberration will be zero at the interface, and will increase in magnitude as the focal plane moves away from the surface, as illustrated in FIG. 5. The change in magnitude (i.e., the slope of the dashed line for surface 58) can be compensated by adjusting the radius of surface 50 so that the spherical aberration produced by surface 50 increases with increasing focal depth. Surface 56 also generates a significant amount of negative spherical aberration, and its magnitude increases with increasing focal depth. The spherical aberrations generated by these three surfaces together, with minor contributions from surfaces 52 and 54 yield the curve labelled "Sum", which is small in both magnitude and slope.

The inner diameter of the contact rim of the contact lens element and the diameter at the end of the contact lens element for contacting the eye are preferably in accordance with U.S. application Ser. No. 09/074,402, the disclosure of which is herein incorporated by reference in its entirety.

Preferred materials for the one or more lens components of the contact lens element include glasses such as "K10", "LaK 9", "Lak 23", "LaK 31", "BK7", "SK54", "SF4", "SF8", "SF15", "SFL6", and "LaSFN31" available from Schott Glass Technologies, Inc., Duryea, Pa., silica, and plastics such as polymethyl methacrylate (PMMA).

The separate lens components may be assembled by adhesive bonding through use of optical cements such as Norland Optical Adhesives available from Norland Products Inc., New Brunswick, N.J.

The steps outlined above are typically preliminary to the optimization of the design, which may be implemented by using a lens design program such as OSLO (Sinclair Optics, Fairport, N.Y.). The program allows two or more configurations of a design to be optimized. For example, the two configurations can be two different separations between the two lens groups, and the corresponding two focal points at different depths. The optimization can begin by starting with one configuration corresponding to the center of the desired range. Once the optimization produces a design that has the desired image quality, numerical aperture and focal depth, then two configurations for slightly displaced focal depths can be optimized. These two focal depths can be incrementally separated to increase the range. The process can be continued until the required range is achieved, or until the image quality at some point in the range becomes unsatisfactory.

The optimization process does not need to be constrained by the conditions mentioned above, such as second surface 56 being precisely concentric with the incident rays, or adjacent lens components that have exactly the same index of refraction. The optimization program can often improve on these general guidelines, including the selection of alternative lens component materials.

The above discussion generally describes the contact lens element and one aspect of the design process for the contact lens element. The following discussion describes the contact lens element and design process for the contact lens element 40 in more detail, including a discussion of an exemplary contact lens element.

Referring again to FIG. 3, the spherical aberration introduced by surface 58 can be minimized by choosing an index of refraction for the glass that is as close as possible to that of the tear layer 60, which is approximately 1.336. The glass chosen for the exemplary lens component 48 was fused silica, having an index of refraction of 1.458.

For the variable focus lens assembly, the change in spherical aberration (SA) that occurs with change of depth is equally troublesome as the absolute value. As mentioned above, one method to produce a compensating change of SA is to adjust the radius of surface 50 so that its SA changes with depth in the opposite direction relative to surface 58.

FIG. 5 graphically shows how the SA of the different surfaces of the contact lens element 40 may be balanced out, where the line labeled Surf. 58 illustrates the SA from surface 58, and the line labeled Surf. 50 illustrates the SA from surface 50. As the distance between the contact lens element 40 and the objective 30 decreases, the SA of surface 50 changes in the opposite direction from that of surface 58. Surface 56 also contributes a significant amount of spherical aberration. The amount of SA from surfaces 52 and 54 are relatively small. When the contributions from all surfaces 50, 52, 54, 56, and 58 are combined, the result is the curve labeled SUM.

The extended range of the present design is achieved by utilizing two optical design principles. As noted above, the variation of SA is controlled largely by utilizing the known variation of SA as a function of the object distance relative to a spherical glass surface. The SA curve shown at FIG. 4, which is based on FIG. 56 of KINGSLAKE, cited above, shows a local maximum positive value 110, which may be a maximum positive value, when the radius (r) of surface 50 is about:

$$r = 1.2 * r_{apl} \quad (eq. 1)$$

where $r_{apl}$=the aplanatic radius for the particular index of the glass:

$$r_{apl} = L/(1+n) \quad (eq. 2)$$

where n=index of refraction of the glass, and L=the distance from the surface to the point of convergence of a bundle of rays entering the surface.

Before the optimization of the design was undertaken, an initial value for the radius of curvature (r) of surface 50 was selected. The radius of curvature (r) was chosen so that the slope of the line representing SA vs. separation distance was equal in amplitude but opposite in sign to the slope for surf. 58. The reasons for varying surface 50 were:

(1) The radius of surface 58 could not be significantly modified because surface 58 contacts the cornea along its rim to maintain a small thickness of tears 60 at the center of the contact lens element 40.

(2) The focus of the light (the focal plane) is very close to surface 58, at one end of the desired focal range. When the focus is at this surface it generates zero SA. As the focus moves away from surface 58, negative SA is generated and the magnitude increases with distance. Therefore, surface 58 will always generate SA that increases in (negative) magnitude with increasing depth in the cornea.

On the basis of the above criteria an initial radius of 12.0 mm was chosen for the exemplary surface 50. Lens component 42 was chosen to be "LaK33" glass available from Schott Glass Technologies, Inc., Duryea, Pa.

After optimization the radius of curvature of the exemplary surface 50 was 9.999 mm. The SA curve for the exemplary surface 50 is shown in FIG. 5.

The radius of curvature for exemplary surface 50 does not satisfy the aplanatic condition (eq. 2) or the condition for maximum positive SA (eq. 1). Rather, the radius of curvature of surface 50 (r=9.999 mm) has the following values relative to the aplanatic radius, $r_{apl}$:

| L | $r_{apl}$ | $r/r_{apl}$ |
|---|---|---|
| 16.6 mm | 6.0276 mm | 1.66 |
| 19.4 mm | 7.0444 mm | 1.41 |

If the maximum positive SA condition were desired, the ratio $r/r_{apl}$ would be 1.2.

Other surfaces in the lens assembly (particularly surface 56) can also generate SA. The optimum radius of curvature for surface 50 is determined by the SA's of all the other surfaces as well as the balancing of chromatic aberration by all surfaces. Hence, the optimization algorithm preferably determines the final radius of curvature of surface 50 along with the radii of curvature of other surfaces as well as the thicknesses of the lens components. But the starting point for the design and optimization preferably includes a radius of curvature for surface 50 that has an SA slope opposite to that of surface 58 and nearly equal in magnitude. This factor suggests using the portion of the curve in FIG. 4 between points 108 and 110, where the slope is positive. The starting point for the optimization was in this portion of the curve.

Figure 7:
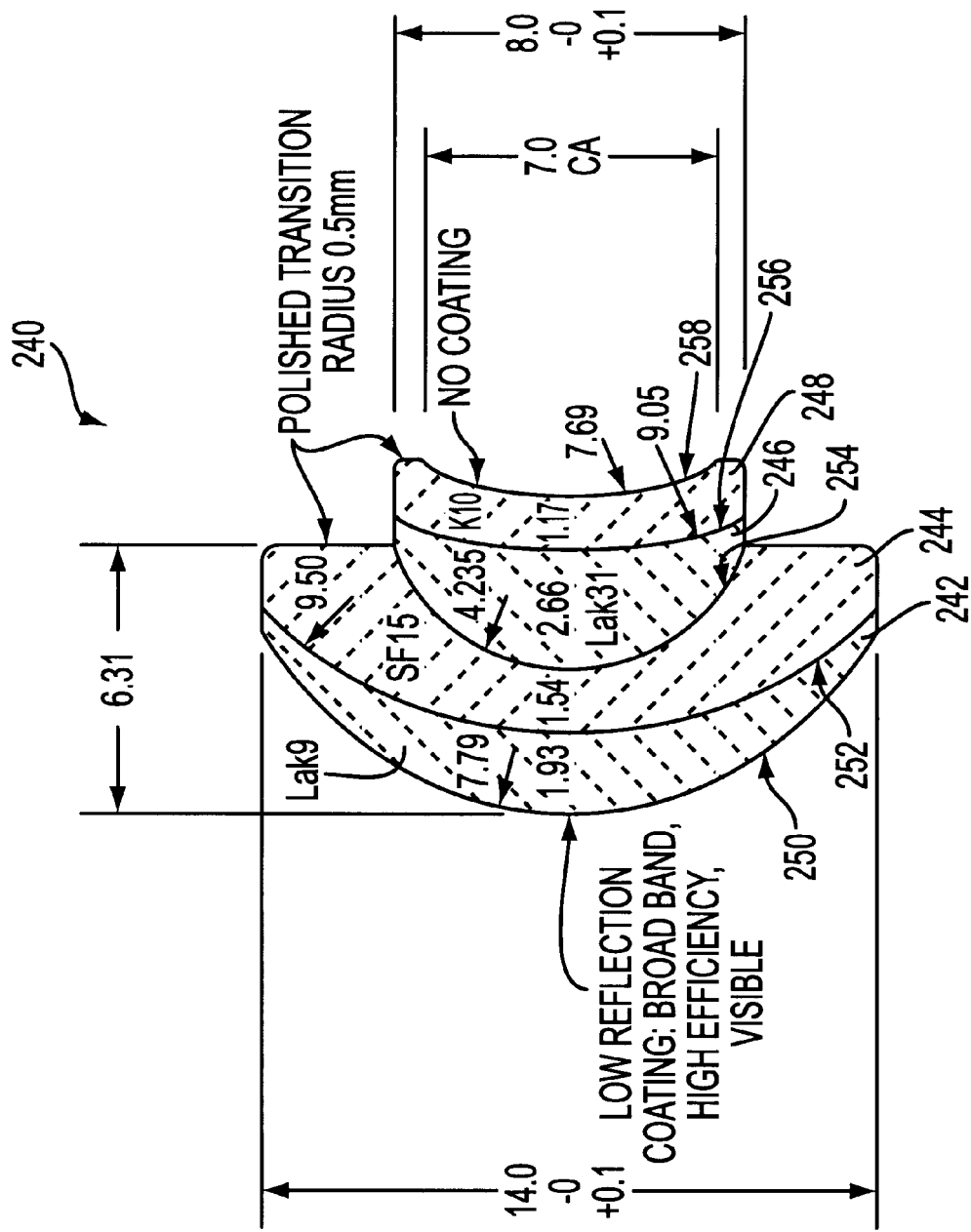
FIG. 7 is a cross-section of an embodiment of the contact lens element for examining the anterior portion of the crystalline lens of the eye.

For comparison purposes, FIG. 7 shows a contact lens element 240 for use with a Nikon 20X, NA 0.35 objective for examining the anterior portion of the crystalline lens with all dimensions shown in millimeters. In FIG. 7, elements which correspond to elements of the embodiment of FIGS. 1–3 are labelled with reference characters which are 200 higher than the respective elements of FIGS. 1–3.

Table 1 below shows the compositions and radii of curvature of the lens components of contact lens elements 40 and 240. Table 1 also shows the refractive indices of the lens components of contact lens elements 40 and 240 which were used to plot FIG. 8 described below. In Table 1, many of the compositions refer to glasses available for Schott Glass Technologies, Inc., Duryea, Pa. Also in Table 1, "Radius" refers to the radius of curvature; "RN1", "RN2", and "RN3" refer to the indices of refraction at the wavelengths 587.6 nm, 486.1 nm, and 656.3 nm, respectively; and "VNBR" refers to the Abbe ν number.

TABLE 1

| Surface | Composition | Radius (mm) | Thickness (mm) | RN1 | RN2 | RN3 | VNBR |
|---|---|---|---|---|---|---|---|
| | | | Lens 40 | | | | |
| | Air | — | — | 1.00 | 1.00 | 1.00 | — |
| 250 | LAK33 | 10.00 | 3.26 | 1.75 | 1.76 | 1.75 | 52.4 |
| 252 | LASF33 | 13.78 | 2.20 | 1.81 | 1.82 | 1.80 | 34.2 |
| 254 | LASFN30 | 3.85 | 5.83 | 1.80 | 1.82 | 1.80 | 46.4 |
| 256 | SILICA99 | 6.38 | 1.47 | 1.46 | 1.46 | 1.46 | 67.8 |
| 258 | aqueous | 7.69 | 0.01 | 1.34 | 1.34 | 1.33 | 55.2 |
| | cornea | 7.77 | 0.77 | 1.38 | 1.38 | 1.37 | 63.3 |
| | | | Lens 240 | | | | |
| | Air | — | — | 1.00 | 1.00 | 1.00 | — |
| 350 | LAK9 | 7.79 | 1.93 | 1.69 | 1.70 | 1.68 | 54.7 |
| 352 | SF15 | 9.50 | 1.54 | 1.70 | 1.72 | 1.69 | 30.1 |
| 354 | LAK31 | 4.23 | 2.66 | 1.70 | 1.71 | 1.69 | 56.4 |
| 356 | K10 | 9.05 | 1.17 | 1.50 | 1.51 | 1.50 | 56.4 |
| 358 | aqueous | 7.69 | 0.10 | 1.34 | 1.34 | 1.33 | 55.2 |
| | cornea | 7.77 | 0.50 | 1.38 | 1.38 | 1.37 | 63.3 |
| | aqueous | 6.80 | 3.84 | 1.34 | 1.34 | 1.33 | 55.2 |

In view of the above, Table 1 shows the compositions, indices of refraction, and resulting Abbe ν numbers. For example, by comparing surfaces 352 and 354, it is apparent that compositions that have similar indices of refraction can result in large differences in dispersion.

Figure 8:
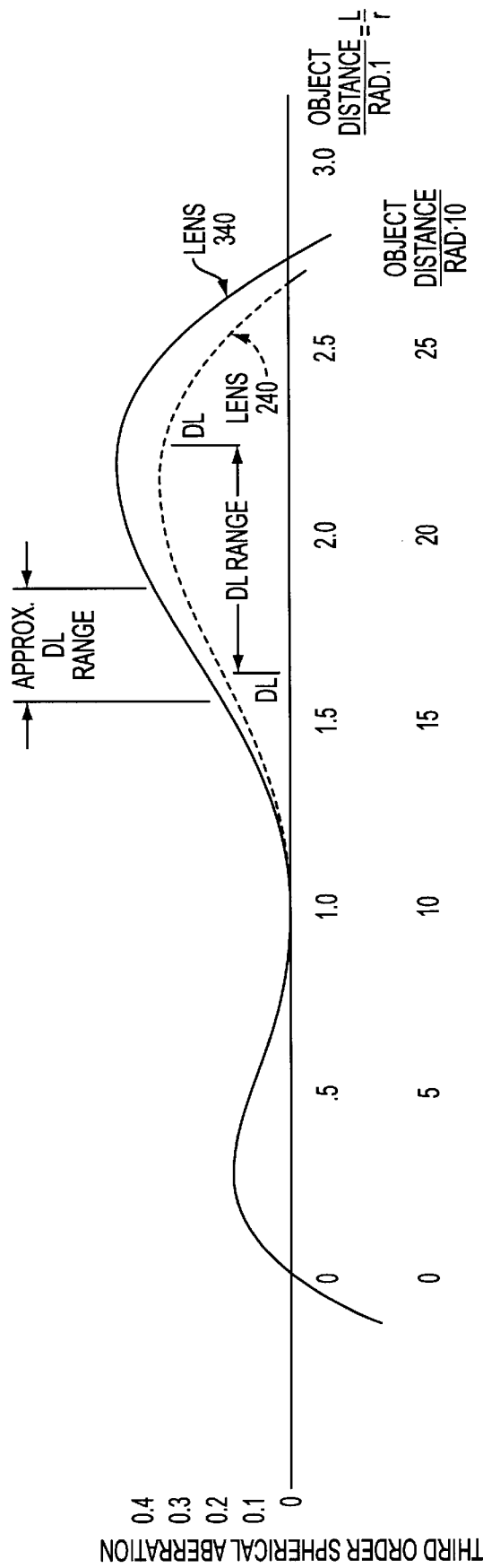
FIG. 8 is a graph showing spherical aberration for the embodiment of FIGS. 1–3 and the embodiment of FIG. 7 in a range of focus in which spherical aberration is predominantly positive in sign and changes slowly with changes in focal depth.

FIG. 8 plots the spherical aberration generated by the first surface 50 of contact lens element 40 and the first surface 250 of contact lens element 240. The horizontal axis represents the ratio L/r, where r is the radius of the first surface and L is the object distance, i.e., the distance from the spherical surface to the point at which the rays would come to focus in the absence of the contact lens element.

The range of focus obtained by contact lens element 40 corresponds to the portion of the curve for lens 40 which was marked "DL range". The range is located entirely on the portion of the curve having a positive slope.

In contrast, contact lens element 240 for imaging the crystalline lens did not have this same requirement. The rays passing through the cornea and the adjacent surface 258 did not produce a spherical aberration curve that went through zero and increased linearly with focal distance, but was more gradual in its variation with focal depth. As a result, the portion of the curve that was most useful was a region that included the maximum and the gradual slope to the left of the maximum.

As noted above, the ranges over which the contact lens elements 40 and 240 are to be used are marked by vertical lines. For contact lens element 40 for examining the cornea, the diffraction limited range is approximately $1.57 \leq L/r \leq 1.87$. For contact lens element 240 for examining the crystalline lens, the diffraction limited range is approximately $1.63 \leq L/r \leq 2.24$. Although the variable focus lens assembly may be designed to be adjusted in areas outside the diffraction limited range, the variable focus lens assembly may also be designed so that the objective and the contact lens element may not be adjusted outside of the diffraction limited range.

In the case of examining the crystalline lens, the range includes the maximum of the curve, which occurs at a value of $L_p = r(1+n)/1.2$ where n is the index of refraction of the glass. See KINGSLAKE, cited above, p. 107. Including the maximum of the curve in the range is often valuable because the spherical aberration is nearly constant as the set point is moved from one side of the maximum to the other. In the example of the contact lens element 240, a glass with an index of refraction of 1.691 was used as the first lens component 242; in this case the maximum peak of the curve occurs at:

$$L_P = \frac{r \cdot (1 + 1.691)}{1.2} = 2.24 \cdot r$$

Other compositions could also be used for the first lens component 242 in the contact lens element, depending on a number of possible requirements, e.g., desired NA depth at which the image is to be obtained, cost of the glass, etc. Table 2 summarizes the ratio L/r for the designs cited and for the range of indices of refraction for available glasses.

TABLE 2

| Values of L/r |  |
|---|---|
| A. Over the range of two designs | |
| Contact Lens Element | L/r |
| 40 | 1.57 to 1.87 |
| 240 | 1.63 to 2.24 |
| B. Values of L/r that include the maximum of the overcorrection curve, L/r = (1 + n)/1.2 | |

TABLE 2-continued

Values of L/r

| Index of Refraction (n) | L/r |
|---|---|
| 1.437 ("SK54" glass) | 2.03 |
| 2.02 ("La SF 35" glass) | 2.52 |

Thus, Table 2 shows that selection of the glass affects the L/r value and shows values of L/r that may be obtained.

As noted above, the chromatic aberration is controlled by utilizing two lens components (44 and 46 of FIGS. 1–3) with nearly the same index of refraction, but very different indices of refraction. This principle of a "buried" chromatic correcting surface is disclosed in U.S. Pat. No. 576,896 to RUDOLPH. In the design of the present lens systems, it has been found that with the proper choice of curvature of the cemented surface and the choice of the two glasses, the change in chromatic aberration for surface 54 and 50 can be made approximately equal in magnitude and opposite in sign over the desired range of focus. FIG. 6 illustrates this situation for the design of FIG. 3. Finally, the optimization program expediently adjusts the radii of curvature and thicknesses of all components to produce the minimum sum of chromatic aberration for the assembly.

In particular, FIG. 6 shows a chromatic aberration curve in which surface 50 generates substantial chromatic aberration (CA), which increases as the depth of the focal plane in the cornea is increased. Surface 54 is the interface between lens component 44 which has a high dispersion and lens component 46 which has approximately the same index of refraction but has a lower dispersion. The materials of exemplary lens components 44 and 46 are "LaSF33" and "LaSFN30" glasses available from Schott Glass Technologies, Inc., Duryea, Pa. Surface 54 produces a substantial amount of positive CA that nearly balances the negative CA produced by surface 50. Furthermore, the magnitude of the CA of surface 54 increases with increasing depth of the focal plane at about the same rate as that for surface 50. The curve labeled "Sum" shows the combined effect of all surfaces, 50, 52, 54, 56, and 58. The CA contributions of surfaces 52, 56, and 58 are minor.

The overall performance of the system is evaluated by two criteria:

(1) The size of the spot formed at the focal plane when rays of three wavelengths (red, green, and blue) are traced through the system. Specifically, the program calculates the distance to each ray from the geometrical center of the spot, and computes the root mean square (RMS) of these distances. A benchmark for comparison is the radius of the Airy disc for an image having the same NA as the system being evaluated.

(2) The optimization program also calculates the degree to which the wavefront that comes to focus at the focal plane deviates from a perfect spherical surface. The RMS OPD (optical path difference) is the root mean square of the irregularities in the wavefront, measured in wavelengths at 587.6 nm. A generally accepted criterion is that an RMS OPD of 0.075 or less indicates a diffraction limited wavefront. This evaluation utilizes only monochromatic light and therefore does not take into account chromatic aberration.

For the present optical systems, the goal of the design is to have the image meet both criteria over the required range of focus, i.e., RMS spot radius<Airy radius, and RMS OPD<0.075 wavelength.

Figure 9:
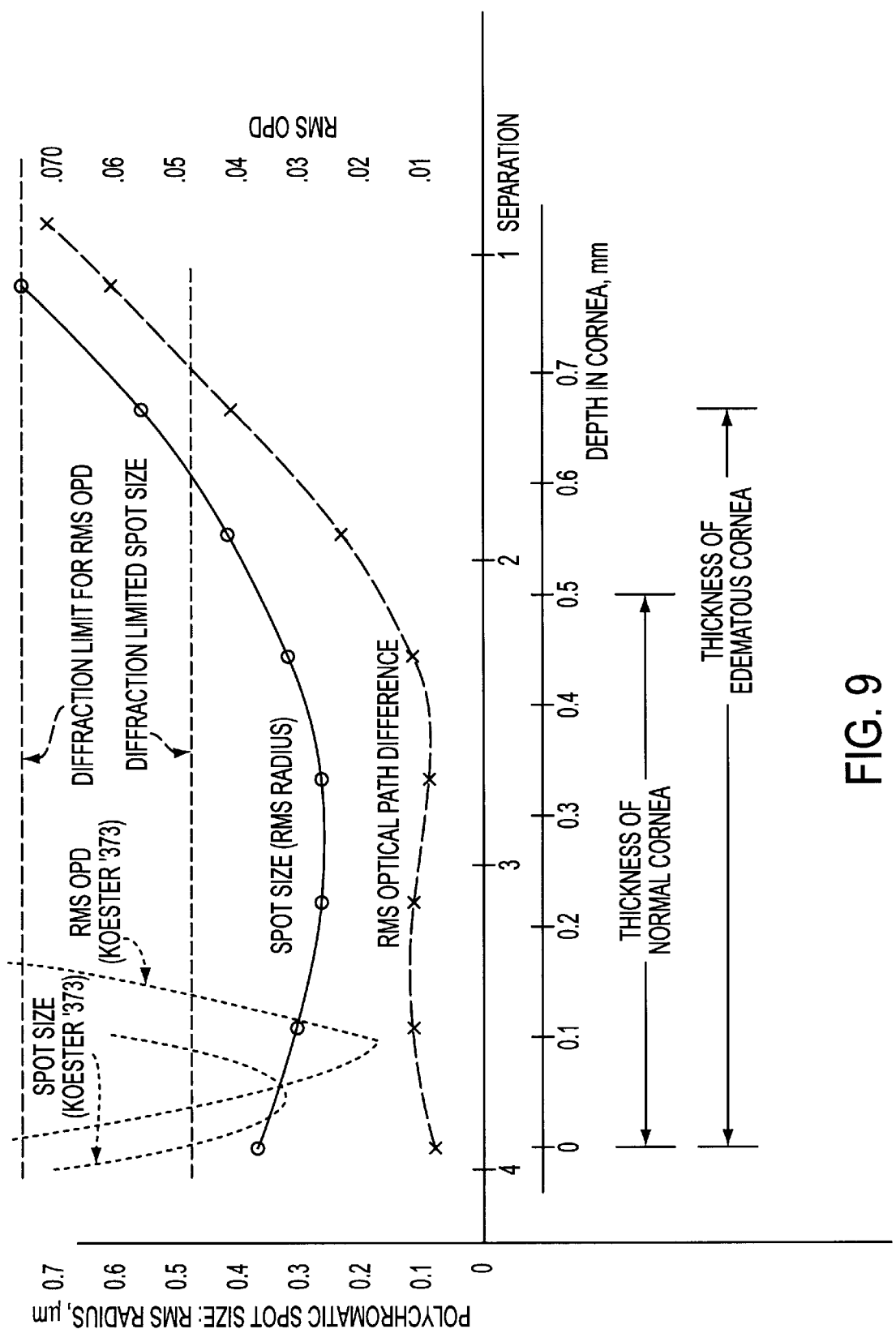
FIG. 9 is a graph comparing the optical performance of a variable focus lens assembly using the contact lens element of FIGS. 1–3 with the optical performance of a fixed focus lens assembly using a known contact lens element.

FIG. 9 shows data directed to RMS spot radius and RMS OPD for the embodiment shown in FIGS. 1–3 for examining the cornea. The solid line represents the spot size (RMS radius) that is generated for the 3 wavelengths of 656.3 nm, 587.6 nm, and 486.1 nm as the separation between the contact lens element 40 and objective 30 is varied from 4 to 1 mm. The horizontal axis is also labeled with the corresponding depth of the focal plane in the cornea, from 0 to 0.7 mm. The curve labeled "spot size" indicates that the image is less than the diffraction limited spot size from the surface of the cornea (depth=0) to a depth of about 0.6 mm. The RMS OPD is also below the 0.075 value, and therefore is also DL (diffraction limited).

For comparison, the two dashed curves at the left represent the performance of an earlier design for examining the cornea in accordance with U.S. Pat. No. 5,359,373 to KOESTER et al., the disclosure of which is herein incorporated by reference in its entirety. The NA of this design was 0.71. This design also produced DL performance, but only over a range of depth of about 0.1 mm.

In addition to being used to examine the cornea, as noted above, the present invention may be used to examine other transparent and semi-transparent objects. For instance, the present invention may be modified to examine the crystalline lens. The following paragraphs discuss embodiments for examining the crystalline lens.

Referring again to the embodiment of FIG. 7, contact lens element 240 is for examining the anterior portion of the crystalline lens. The design process for contact lens elements 240 for examining the crystalline lens or iris is similar to the design process for examining the cornea. In this case the range of focus is needed not only to image at various depths within the tissue, but also to accommodate the differences in eye sizes in the population. In particular, the anterior chamber depth, the distance between the posterior corneal surface to the anterior surface of the lens, varies from about 2.3 mm to about 4.1 mm in the adult population.

In designing contact lens elements for examining the crystalline lens, the contact lens element may be initially optimized for one focal distance only. The next design phase is to optimize the design for two focal distances separated by a small distance, e.g., about 0.1 mm. In general terms, this is called optimization for two configurations. When this optimization is successful for a small separation between the contact lens element and objective, the separation can be increased to, e.g., about 0.2 mm and the optimization procedure is then repeated. Each optimization alters the radius of curvature of each surface that is designated as a variable, also the thickness of each lens component that is designated as a variable.

When the separation between focal points has been increased to about 0.5 mm, it is useful to calculate the performance of the system over the desired range of focal distances. The performance is preferably diffraction limited at all points between the selected focal points. When this is the case, the above procedure can be continued, i.e., increasing the separation between focal points and re-optimizing.

The above steps can be repeated until the performance is no longer diffraction limited at some point or points at or between the selected focal points. This result indicates that the range of this overall design cannot be further expanded, unless certain constraints can be relaxed or different lens component compositions can be chosen. Examples of constraints that might be relaxed are the thickness of certain components and the curvature of the surfaces. In optical design programs that allow the index and dispersion of glasses to be varied during optimization, this feature can be used to find or suggest new glasses to utilize in the design. After new glasses have been selected and the constraints have been adjusted, the iteration of focus separation and optimization can be continued. Finally, if the desired range of focus has not been reached, one option is to decrease the target value of the numerical aperture. Another option is to start with a design containing additional components in order to increase numerical aperture, for example.

Figure 10:
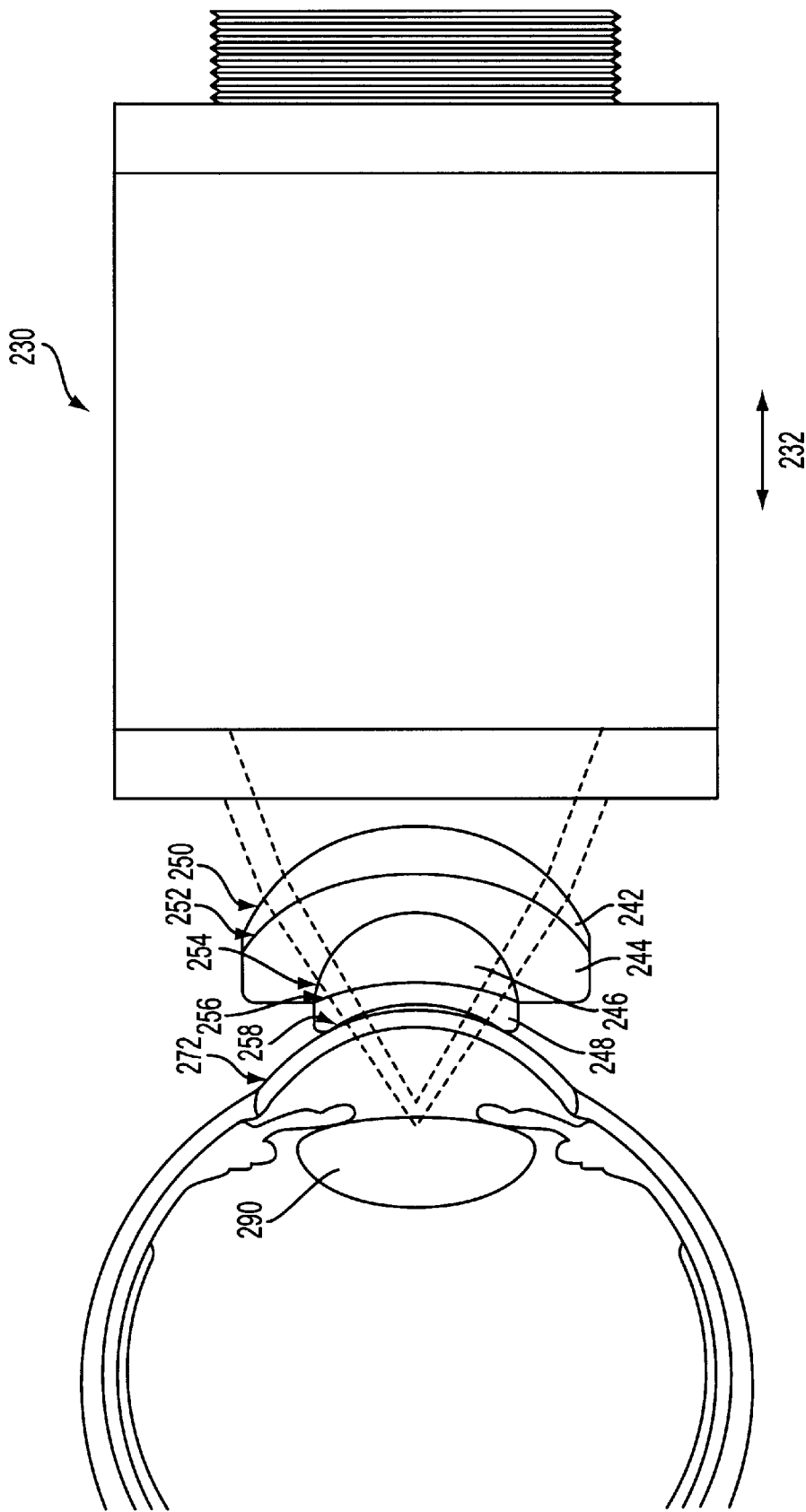
FIG. 10 is a schematic illustrating a variable focus lens assembly for examining the crystalline lens of the eye, which includes the contact lens element of FIG. 7.

In the embodiment shown in FIGS. 7 and 10, surface 258 is not close to the focal point. Surface 258 contributes significant negative SA, as does surface 256. In this case the positive SA from surface 250 needs to be at or near its maximum value, which occurs at the radius:

$$r=1.2 * r_{apl}$$

The optimization program selects the radius of curvature of surface 250 to satisfy this equation at a point that is within the range of the adjustment between the objective and contact lens element.

Figure 11:
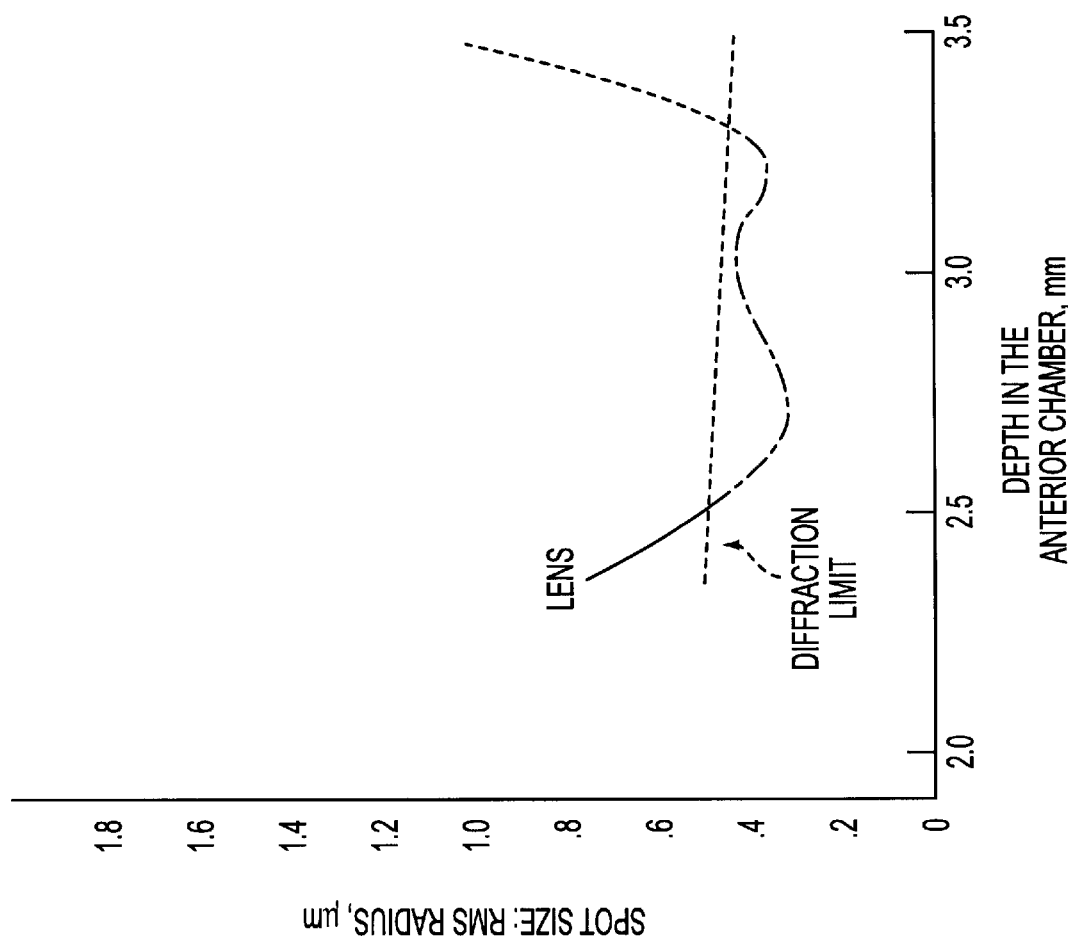
FIG. 11 is a graph showing the optical performance of a variable focus lens assembly including the contact lens element of FIG. 7.
Figure 12:
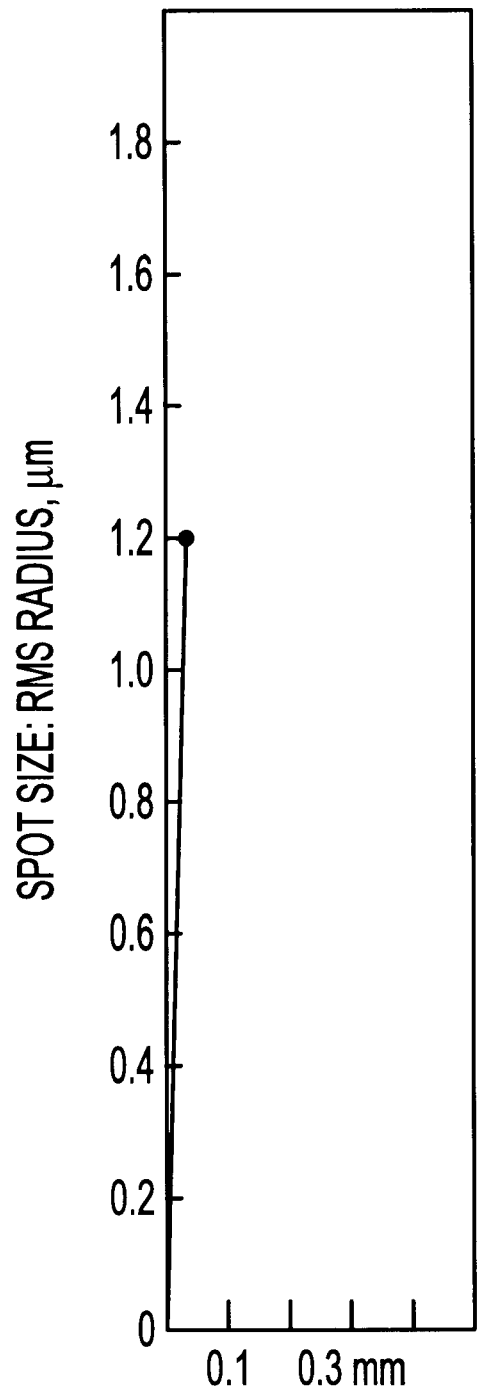
FIG. 12 is a graph showing the optical performance of a known objective without a contact lens element.

Referring to FIG. 11, the combination of contact lens element 240 and a Nikon 20X, NA 0.35 objective yielded a diffraction limited performance at NA 0.80 over a range of AC depths of 2.5 mm to 3.3 mm. This range covers the central 80% of the distribution of AC depths in the adult population. In FIG. 11, the X axis represents the depth in the anterior chamber, and the Y axis represents the spot size on the retina of a point source at infinity, using ray tracing at the 3 wavelengths of 656.3 nm, 587.6 nm, and 486.1 nm to generate the spot diagram. The numerical values represent the root mean square (RMS) radius of the spot. For comparison, the dashed line represents the radius of the Airy disc. Points on the curve that are below the Airy disc line represent images that are diffraction limited, i.e., the best that can be achieved given the NA of the objective and the wavelength of the light. In comparison, FIG. 12 shows the spot size for a normal objective (i.e., without a contact lens element), NA 0.8, focused on the cornea.

Figure 13:
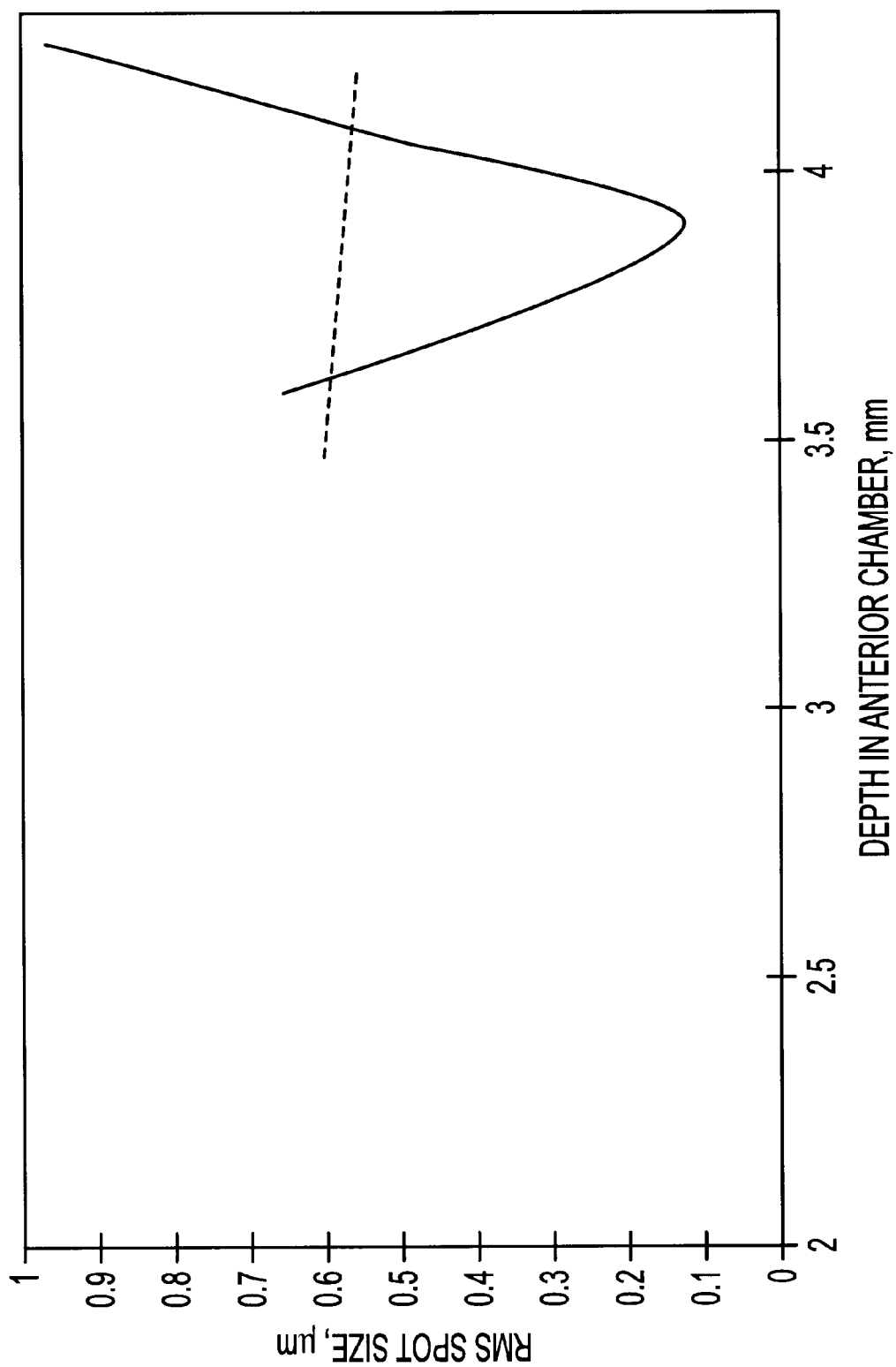
FIG. 13 is a graph showing the optical performance of a lens assembly including a contact lens element that has not been optimized for an extended range of focus.

The advantage of contact lens element 240 which has been optimized for a range of focal points, over a contact lens element that has been optimized for only one focal depth is made apparent by comparing FIGS. 11 and 13. In particular, FIG. 13 illustrates the image quality yielded by a combination of a contact lens element with a Nikon 20X, NA 0.35 objective is shown over a range of about 0.7 mm. In this case the contact lens element is optimized for a single working distance of about 3.9 mm, and it is diffraction limited over a range of only 0.45 mm. It is noted that the minimum spot size of FIG. 13 is smaller than the minimum spot size of FIG. 11. However, diffraction limits the actual spot size to the value indicated by the dashed lines, so that spot sizes below the diffraction limit do not improve the image significantly.

Figure 14:
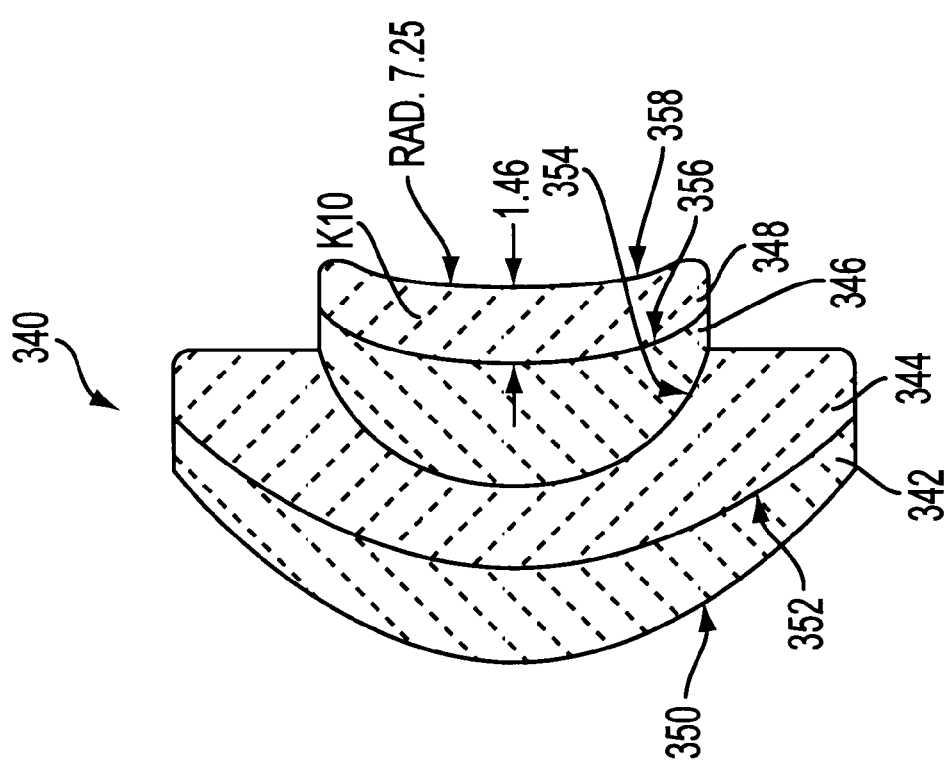
FIG. 14 is a cross-section of an embodiment of the contact lens element for examining the anterior portion of the crystalline lens of the eye for a patient having a shallow anterior chamber.
Figure 15:
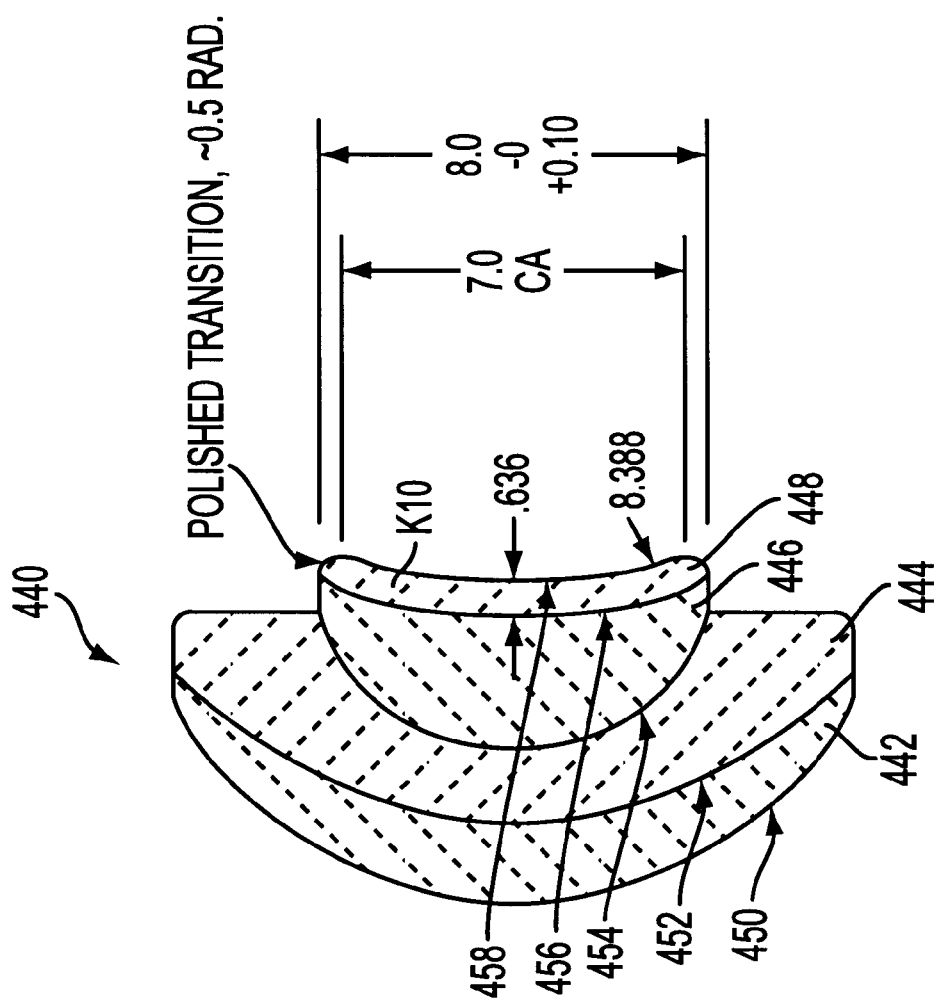
FIG. 15 is a cross-section of an embodiment of the contact lens element for examining the anterior portion of the crystalline lens of the eye for a patient having a deep anterior chamber.

For patients (subjects) with AC depths less than 2.7 mm or greater than 3.5 mm, two modifications of the contact lens element 240 of FIGS. 7 and 10 were designed and fabricated. In particular, FIGS. 14 and 15 illustrate contact lens elements for use with a Nikon 20X, NA 0.35 objective for examining the anterior portion of the crystalline lens with all dimensions shown in millimeters. In FIGS. 14 and 15, elements which correspond to elements of the embodiment of FIGS. 1–3 are labelled with reference characters which are 300 and 400 higher, respectively, than the respective elements of FIGS. 1–3.

Figure 16:
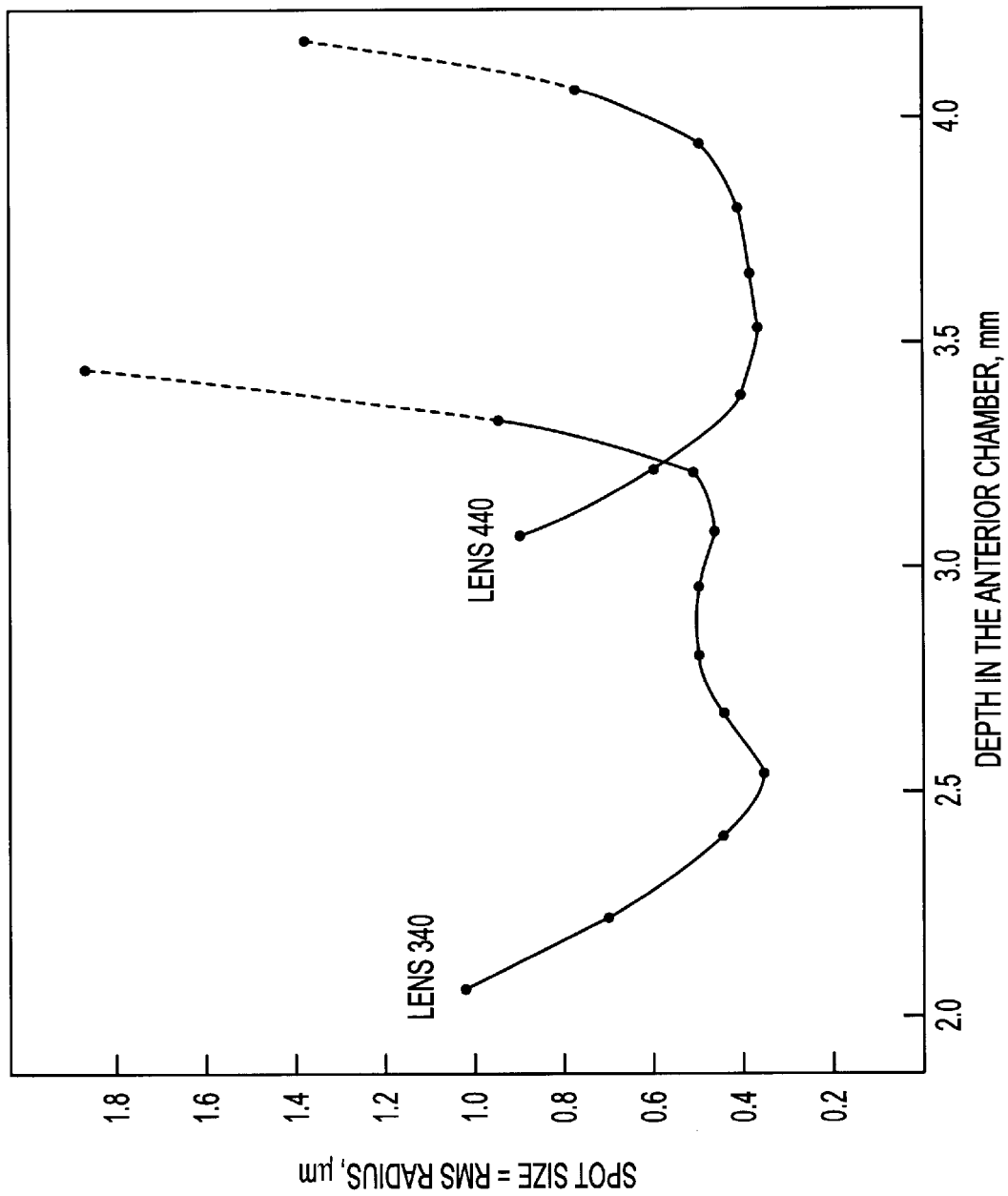
FIG. 16 is a graph showing the optical performance of lens assemblies including either the contact lens element of FIG. 14 or the contact lens element of FIG. 15.

The results of contact lens elements 340 and 440 are shown in FIG. 16. The range of each includes the central AC depth, 3.1 mm. Thus, if the subject is known or suspected of having a short AC depth, contact lens element 340 would be selected. It is also informative to compare the performance of contact lens elements 340 and 440 to a contact lens element that has been optimized for a single focal distance by comparing FIGS. 13 and 16.

From the manufacturing point of view, the contact lens elements 240, 340, and 440 differ only in the thickness and final curvature of the lens component 248, 348, and 448. Thus, the mounts are designed to be readily interchangeable. In other words, lens components 242, 244, and 246 of contact lens element 240, lens components 342, 344, and 346 of contact lens element 340, and lens components 442, 444, and 446 of contact lens element 440 are the same.

Figure 17:
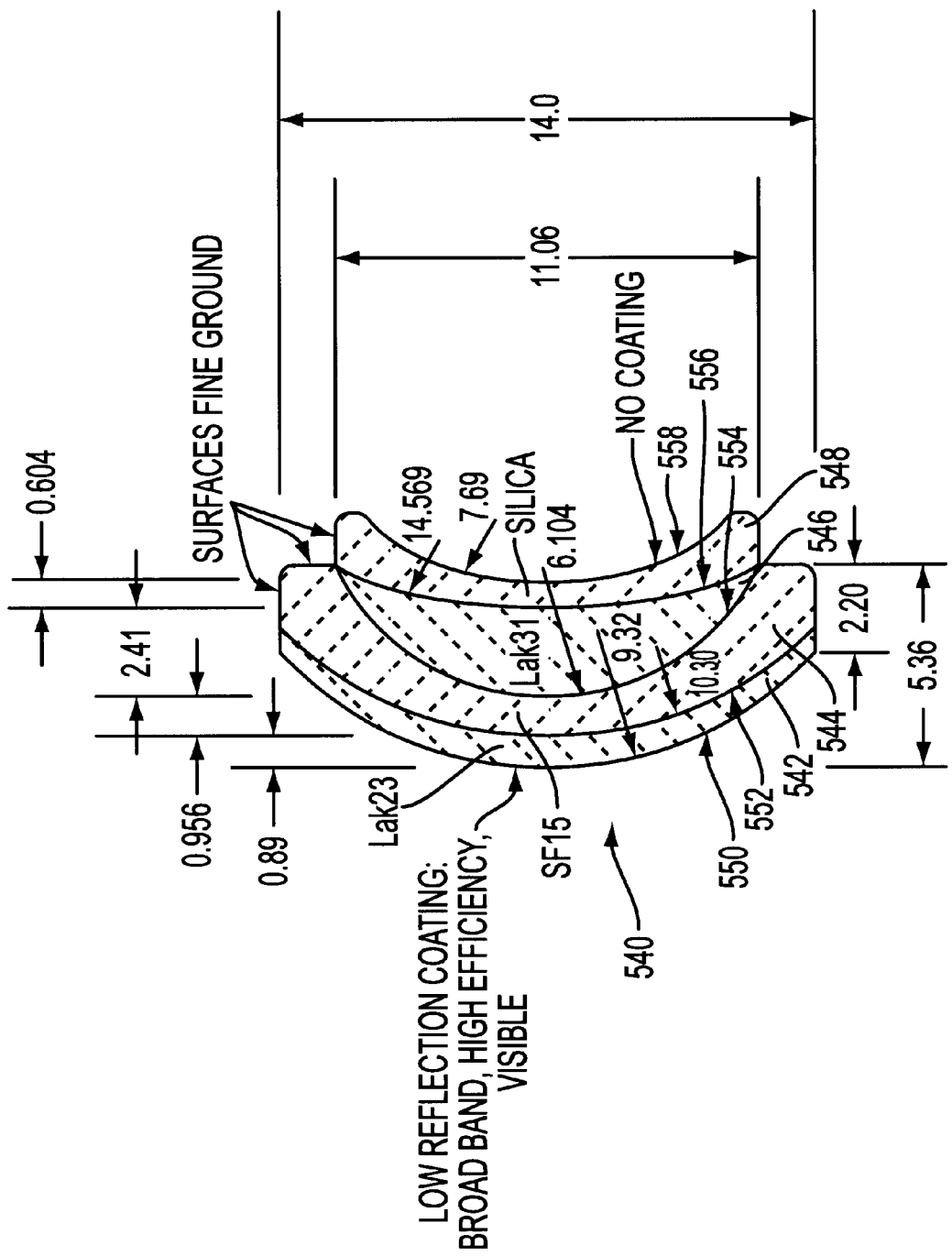
FIG. 17 is a cross-section of an embodiment of the contact lens element for examining the posterior portion of the crystalline lens of the eye.

FIG. 17 illustrates a contact lens element for examining the posterior portion of the crystalline lens with all dimensions shown in millimeters. In FIG. 17, elements which correspond to elements of the embodiment of FIGS. 1–3 are labelled with reference characters which are 500 higher than the respective elements of FIGS. 1–3.

The contact lens element 540 is designed to work with a Nikon 20X, NA 0.35 objective with a working distance of 19.9 mm. Surface 558 of the contact lens element 540 has a radius of curvature of 7.69 mm and contacts the cornea along a polished rim at a diameter of about 7 mm. By holding the contact lens element 540 stationary on the cornea and by varying the position of an objective lens, the focal plane in the eye can be adjusted from a depth of about 2.9 mm to 3.7 mm. The individual lens components that form the contact lens element are formed of silica, "LaK31", "SF15", and "LaK23" glasses available from Schott Glass Technologies, Inc., Duryea, Pa. The low reflection coating is preferably broad band (i.e., covers a broad band width of light), high efficiency (i.e., low reflectance), and visible (i.e., designed for the visible light spectrum).

To image details in the posterior portion of the crystalline lens, the optical system necessarily involves the optics of the lens itself including its gradient index of refraction, as well as the shape of the cornea. The optics of the eye were modeled using data recently published by LIOU et al., *J. Opt. Soc. Am. A.*, Vol. 14, pp. 1684–95 (1997), the disclosure of which is herein incorporated by reference in its entirety.

Figure 18:
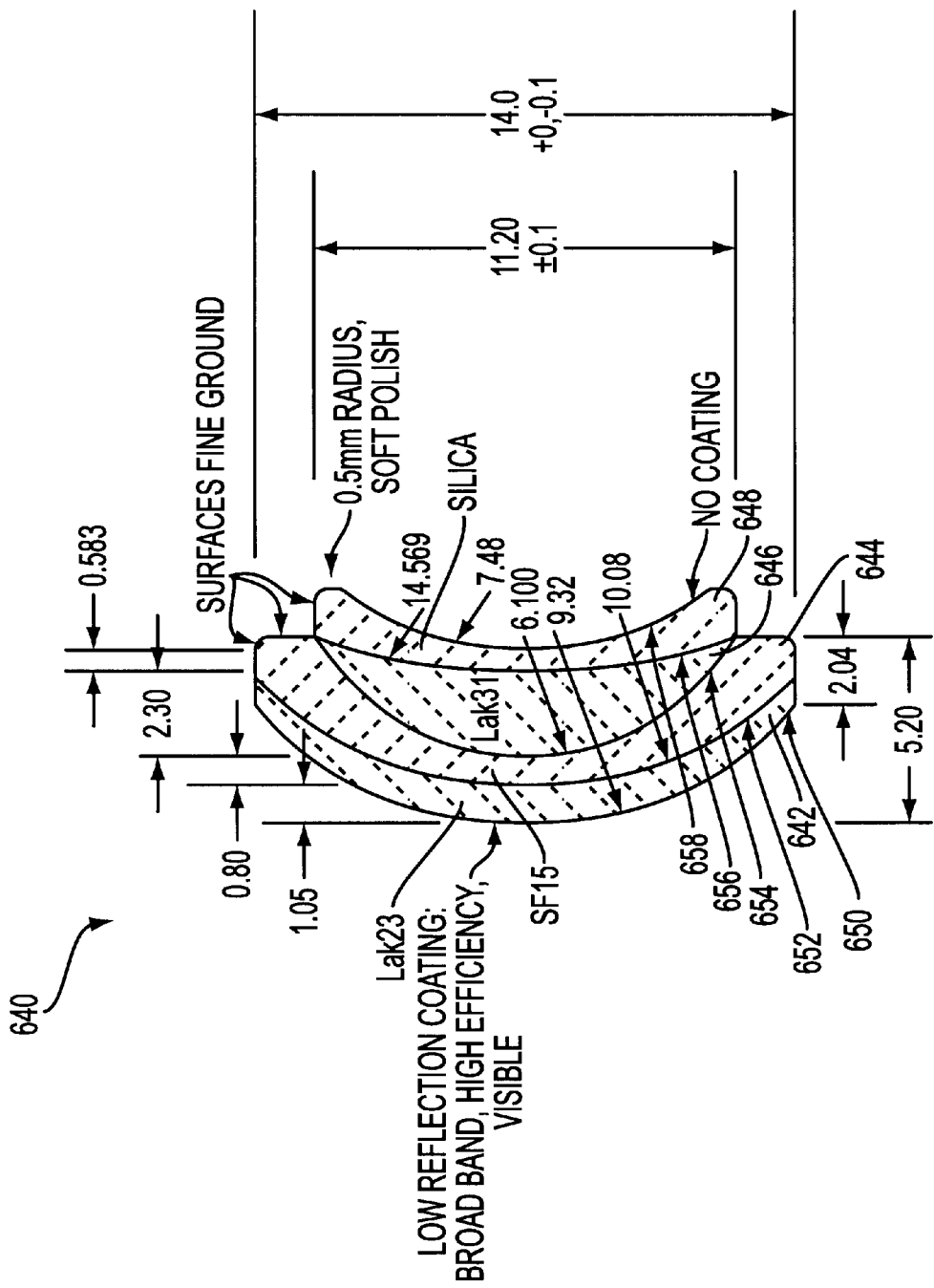
FIG. 18 is a cross-section of an embodiment of the contact lens element for examining the posterior portion of the crystalline lens of the eye for a patient having a deep anterior chamber.
Figure 19:
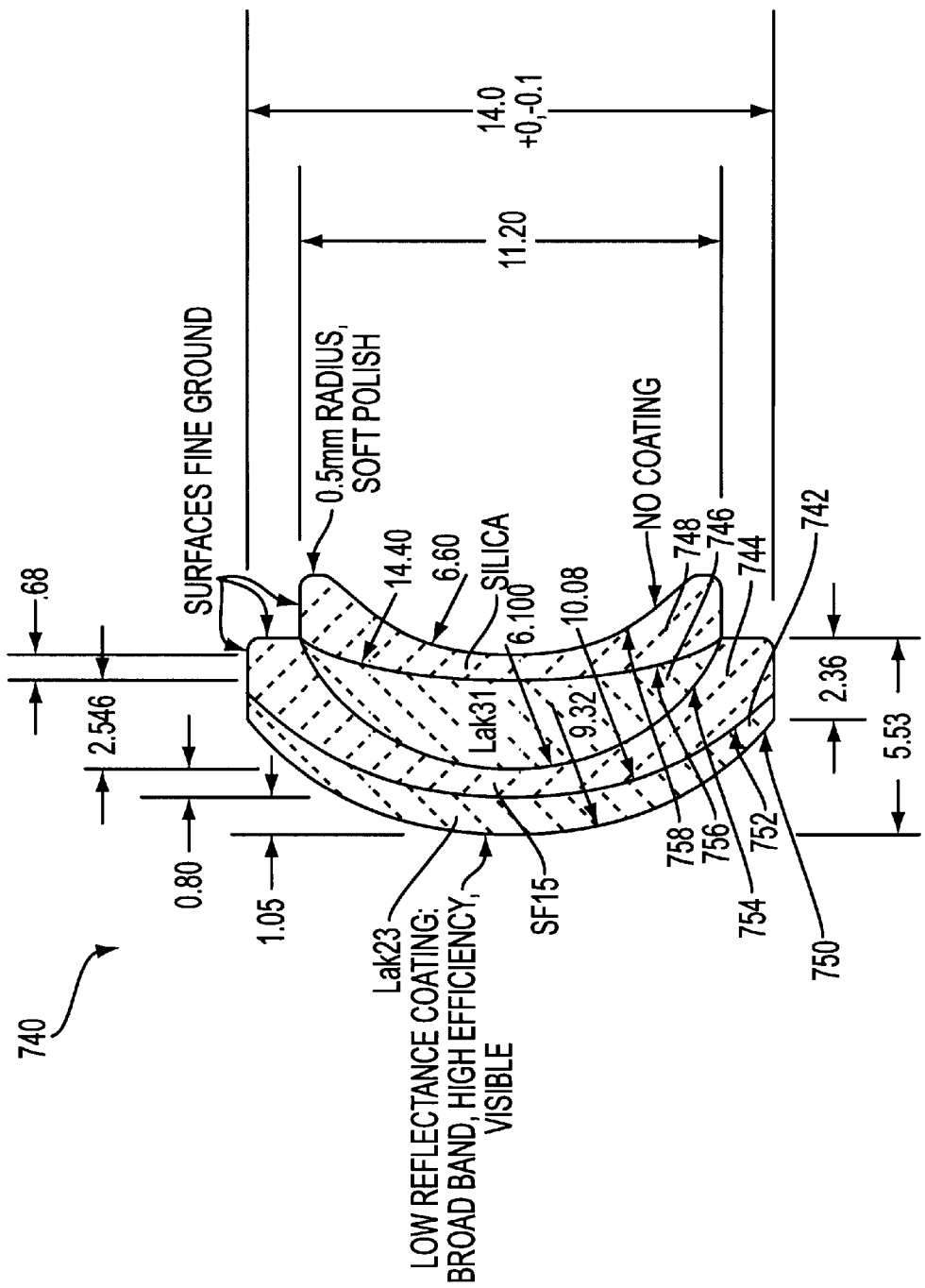
FIG. 19 is a cross-section of an embodiment of the contact lens element for examining the posterior portion of the crystalline lens of the eye for a patient with a shallow or medium anterior chamber depth.

The design of contact lens elements for examining the posterior portion of the crystalline lens is similar to that used for the anterior portion of the crystalline lens, with a working distance about 3.6 mm longer. Two versions of the contact lens element cover the range of AC depths, one from 2.2 to 3.6, the other from 2.8 to 4.0 mm. In particular, FIGS. 18 and 19 illustrate contact lens elements for use with a Nikon 20X, NA 0.35 objective for examining the posterior portion of the crystalline lens with all dimensions shown in millimeters. In FIGS. 18 and 19, elements which correspond to elements of the embodiment of FIGS. 1–3 are labelled with reference characters which are 600 and 700 higher, respectively, than the respective elements of FIGS. 1–3.

Figure 20:
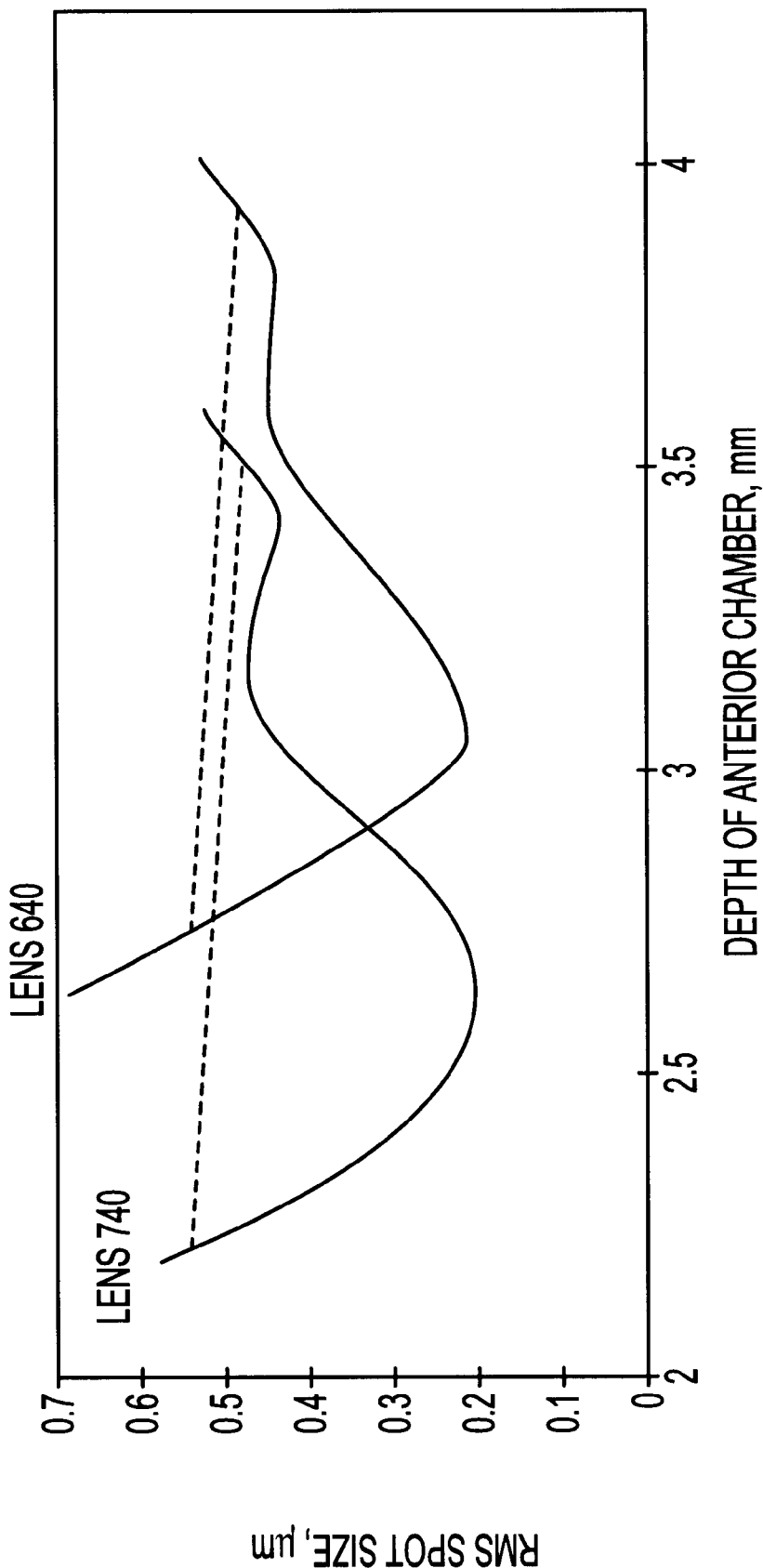
FIG. 20 is a graph showing the optical performance of lens assemblies including either the contact lens element of FIG. 18 or the contact lens element of FIG. 19.

FIG. 20 illustrates the spot size for contact lens elements 640 and 740 of FIGS. 18 and 19. A crystalline lens thickness of 3.6 mm was assumed, and the gradient index of the crystalline lens was assumed to be that published in LIOU et al., *J. Opt. Soc. Am. A.*, Vol. 14, pp. 1684–95 (1997). The dashed lines of FIG. 20 represent the radius of the Airy disc, i.e., the minimum spot radius allowed by diffraction. Together, contact lens elements 640 and 740 provide diffraction limited performance for eyes with anterior chamber depths from 2.2 to 4.0 mm.

It should be noted that there are more uncertainties associated with the design of the contact lens elements for examining the posterior portion of the crystalline lens than for the design that was described above for the anterior portion of the crystalline lens and iris. First of all, the gradient index of the lens was a important part the model. Recent studies utilizing the Shack-Hartmann wavefront sensing technology have shown that the lens has aberrations that vary from subject to subject. Furthermore, in a substantial fraction of the subjects examined, the lens aberrations are greater than the aberrations of the complete eye, and cannot be predicted from aberration measurements of the complete eye. Fortunately, the effect of these aberrations on the image of the posterior lens will be less than if the region being examined were at a greater distance from the variable index region, for example at the retina. Nevertheless, the variability from subject to subject could result in less-than-optimum images in some cases.

Figure 21:
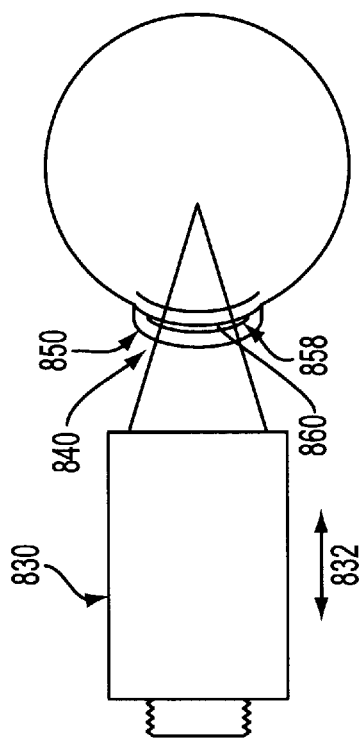
FIG. 21 is a schematic illustrating a variable focus lens assembly in which a contact lens element comprises a single lens component.

FIG. 21 illustrates an embodiment of the invention in which the contact lens element comprises a single lens component. In FIG. 21, elements which correspond to elements of the embodiment of FIGS. 1–3 are labelled with reference characters which are 800 higher than the respective elements of FIGS. 1–3.

Surface 850 is concentric with respect to the rays passing through its surface and therefore produces no spherical or chromatic aberration, for an object point on axis. The second surface 858 of this lens is shaped so that it contacts the cornea along a circular rim that lies outside the optical zone.

The objective 830 produces a converging bundle of illumination rays that are concentric to surface 850. A conventional microscope objective with high NA and long working distance can serve as objective lens 830. To focus the system, objective lens 830 is moved to the left or right as shown by arrow 832 in FIG. 21. For best performance, the center of curvature of surface 850 is on the axis of objective 830, and remain on the axis as the objective lens 830 is moved to change the focus.

A layer of fluid 860, having an index of refraction equal to or greater than that of the tear layer, as discussed in U.S. application Ser. No. 09/074,402 and U.S. Provisional Application No. 60/084,789, the disclosures of which are herein incorporated by reference in their entireties, separates the cornea from surface 858, to reduce or eliminate aberrations that would otherwise be produced by an irregular cornea.

Figure 22:
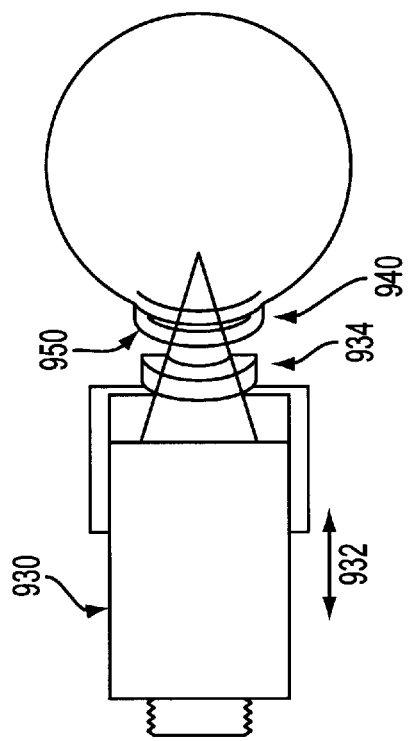
FIG. 22 is a schematic illustrating a variable focus lens assembly which includes an objective, an auxiliary lens, and a contact lens element.

An increase in numerical aperture can be realized by the embodiment illustrated in FIG. 22. In FIG. 22, elements which correspond to elements of the embodiment of FIGS. 1–3 are labelled with reference characters which are 900 higher than the respective elements of FIGS. 1–3.

FIG. 22 is similar to FIG. 21 except that a commercially available long working distance microscope objective lens 930 is combined with a custom designed auxiliary lens 934, such as described in KOESTER '373, cited above, the disclosure of which is herein incorporated by reference in its entirety. The contact lens element 940 has the same design as that of contact lens element 840 in FIG. 21. In FIG. 22, auxiliary lens 934 is an attachment to objective 940 that serves three purposes: (1) to increase the NA of objective 930; (2) to maintain the image quality of objective lens 930; and (3) to provide the working distance that is required by the location of the focal plane in the eye. Although the design process for auxiliary lens 934 is similar to the design process for the contact lens element, the design process for the auxiliary lens element 934 is significantly simpler because the high image quality and the long working distance are required for only one focal distance.

The contact lens elements of FIGS. 21 and 22 may be advantageously hand-held against the cornea for use with slit lamp microscopes (biomicroscopes).

The present invention is also directed to various processes. For instance, the contact lens element of the present invention may be used with diagnostic instruments for examining the cornea or crystalline lens, including the epithelial cells, fiber cells, suture line structures, and early indications of cataract formation such as microscopic opacification. Such diagnostic instruments include biomicroscopes (also known as a slit lamp), fundus cameras, and scanning laser ophthalmoscopes. Similarly, the contact lens element of the present invention may be used with diagnostic instruments for examining the iris for the presence of inflammatory cells or changes due to disease or trauma.

Further, the present invention may be used with therapeutic instruments such as laser photocoagulators or photodisrupters. These instruments typically utilize a slit lamp biomicroscope to locate the area to be treated by the laser, and the laser beam is directed through a portion of the same optical system to the target. Instruments with higher magnification and the greater resolution provided by the present invention may be able to treat smaller lesions, smaller blood vessels, and lesions that are very close to sensitive areas such as the fovea centralis.

Still further, the present invention may be used in conjunction with systems employing adaptive optics to improve images of internal eye structures. Adaptive optics refers to the field of optical systems that can sense the aberrations or other distortions caused by inhomogeneous media such as the atmosphere or the transparent media in the eye, and can then change the shape of a mirror or other optical element in the system so as to correct the aberrations caused by the media. The result is an image of improved quality. One advantage of the present invention involves the stabilization of the eye of the patient or subject while the adaptive optics are being optimized. The contact with the cornea will not prevent all types of eye motion, such as saccades, but it greatly reduces the axial variation in eye position. Because the contact lens element of the present invention greatly reduces aberrations from corneal astigmatism, the amount of correction required of the adaptive optics is reduced.

While the invention has been described in connection with certain preferred embodiments so that aspects thereof may be more fully understood and appreciated, it is not intended to limit the invention to these particular embodiments.

What is claimed is:

1. A variable focus lens assembly, comprising:
a first lens group with positive optical power;
a second lens group with positive optical power;
an adjuster structured to be capable of adjusting a separation between the first lens group and the second lens group; and
wherein the variable focus lens assembly has a numerical aperture greater than about 0.65.

2. The variable focus lens assembly of claim 1, wherein the first lens group comprises a microscope objective having a working distance greater than about 5 mm.

3. The variable focus lens assembly of claim 1, wherein the second lens group is immersed to an object with a fluid having an index of refraction greater than about 1.33.

4. The variable focus lens assembly of claim 1, wherein the adjuster is structured to be capable of adjusting the first lens group along an axis of the first lens group and the second lens group in order to focus the variable focus lens assembly.

5. The variable focus lens assembly of claim 1, wherein the second lens component comprises:
a first lens component having a surface for contacting air, the surface producing chromatic aberration;

a second lens component associated with the first lens component;

a third lens component which is connected along a spherical surface to the second lens component; and wherein the second lens component and the third lens component comprise materials which have indices of refraction which differ by less than about 0.005 and have Abbe ν numbers that differ by more than about 10.

6. The variable focus lens assembly of claim 5, wherein the materials of the second lens component and third lens component have indices of refraction which differ by less than about 0.003 and have Abbe ν numbers that differ by more than about 12.

7. A method of examining or treating one of a transparent and semi-transparent object, comprising:

contacting a distal end of the second lens group of the variable lens assembly of claim 1, with the object to be examined; and examining the object.

8. The variable focus lens assembly of claim 1, wherein the second lens group is positioned closer to an object to be examined than the first lens group, and wherein the first lens group has a numerical aperture of at least about 0.20.

9. The variable focus lens assembly of claim 1, wherein the second lens group is positioned closer to an object to be examined than the first lens group, and wherein the first lens group has a numerical aperture of at least about 0.35.

10. The variable focus lens assembly of claim 1, wherein the second lens group is positioned closer to an object to be examined than the first lens group, and wherein the first lens group has a numerical aperture of at least about 0.40.

11. A variable focus lens assembly, comprising:

a first lens group that is moveable on an axis, the first lens group being well-corrected and having a numerical aperture of at least about 0.20;

a second, fixed lens group sharing the axis of the first lens group;

wherein a distance between the first lens group and the second lens group may be varied over a range;

wherein the variable focus lens assembly has a spot size which is diffraction limited over the range of distance separating the first lens group and the second lens group; and wherein the variable focus lens assembly has a numerical aperture of at least about 0.65.

12. The variable focus lens assembly of claim 11, wherein a proximal surface of the second lens group comprises a radius such that light from the first lens group is incident so that spherical aberration of the proximal surface has a slope relative to focal distance which is less than a slope of spherical aberration relative to focal distance at an aplanatic point, over the range of distance separating the first lens group and the second lens group.

13. The variable focus lens assembly of claim 12, wherein the spherical aberration is near a local maximum overcorrection condition over the range of distance separating the first lens group and the second lens group.

14. The variable focus lens assembly of claim 11, wherein the second lens group comprises two lens components that have indices of refraction that differ by no more than about 0.003 and have Abbe ν numbers that differ by at least 15, the two lens components being connected together along a spherical surface.

15. The variable focus lens assembly of claim 14, wherein the two lens components of the second lens group have indices of refraction that differ by no more than about 0.0025 and have Abbe ν numbers that differ by at least about 22.

16. The variable focus lens assembly of claim 11, wherein a distal surface of the second lens group comprises a circular rim for contacting a cornea of an eye to be examined or treated, the diameter of the circular rim being about 6 to 11 mm.

17. The variable focus lens assembly of claim 11, wherein a distal surface of the second lens group comprises a concave surface having a radius of curvature which is less than that of a cornea of an eye to be examined or treated.

18. The variable focus lens assembly of claim 11, wherein a distal surface of the second lens group comprises one of a flat surface and a convex surface having a radius of curvature which is greater than about 5 mm.

19. The variable focus lens assembly of claim 11, wherein the first lens group and the second lens group comprise a portion of a confocal microscope.

20. The variable focus lens assembly of claim 11, wherein the second lens group is adapted to contact a cornea of an eye along a circular rim of the second lens group.

21. A variable focus lens assembly system for at least one of examination and treatment of ocular tissues, comprising:

an optically clear liquid having a refractive index of about 1.33 to 1.42; and the variable lens assembly of claim 11, the second lens group being capable of holding the liquid against a cornea of an eye to be examined or treated.

22. A method of examining or treating an eye with the variable focus lens of claim 11, comprising focusing on a region within the eye.

23. A method of one of examining and treating body tissue, comprising:

providing a variable focus lens assembly of claim 11, wherein the second lens group comprises a distal surface;

contacting the distal surface of the second lens group with the body tissue; and one of examining and treating the body tissue.

24. The method of claim 23, comprising examination of one of surface detail and subsurface detail of the body tissue.

25. A method of at least one of examining and treating a region within an eye, the eye having a cornea, comprising:

providing a variable focus lens assembly of claim 8, wherein the second lens group comprises a circular rim;

contacting the cornea of the eye with the circular rim of the second lens group; and one of examining and treating the region within the eye.

26. The method of claim 25, wherein the circular rim comprises a diameter which is greater than a diameter of a light beam passing through a surface of the cornea.

27. A variable focus lens assembly, comprising:

a first lens group;

a second lens group associated with the first lens group, the second lens group comprising a first surface having a convex radius r;

wherein a distance between the first lens group and the second lens group may be varied over a range; and wherein the association between the first lens group and the second lens group is such that converging light from the first lens group is focused toward a point at an adjustable distance L inside the first surface of the second lens group, and the ratio L/r is about 1.57 to 2.52 at some point in a range of adjustment of the first lens group relative to the second lens group.

28. The variable focus lens assembly of claim 27, wherein the first surface of the second lens group has chromatic aberration, and wherein the second lens group comprises two lens components that are connected to each other along a spherical surface, the materials of the two lens components having indices of refraction which differ by less than about 0.003 and having Abbe ν numbers that differ by more than about 12.

29. A method for examination or treatment of the eye, comprising:

provliding a system comprising a contact lens element having a recess capable of holding a volume of liquid against a cornea of an eye to be examined or treated, and a microscope unit adjustably connected to the contact lens element;

placing the contact lens element on the cornea to form a substantially enclosed space between the contact lens element and the cornea;

at least one of filling the substantially enclosed space with liquid and allowing the substantially enclosed space to become filled with liquid; and adjusting the position of the microscope unit to focus an image while the contact lens element remains substantially stationary against the cornea.

30. The method of claim 29, wherein the microscope unit comprises a microscope comprising an external lens, and a lens rigidly connected to the external lens of the microscope.

31. The method of claim 29, wherein the microscope unit comprises a microscope objective.

32. The method of claim 29, wherein the contact lens element maintains the eye in substantially the same longitudinal position.

* * * * *